United States Patent
Rajfer et al.

(10) Patent No.: US 10,426,812 B2
(45) Date of Patent: Oct. 1, 2019

(54) COMPOSITIONS AND METHODS FOR THE TREATMENT OF ORTHOPEDIC AILMENTS

(71) Applicant: K.L.R.M., LLC, San Pedro, CA (US)

(72) Inventors: Jacob Rajfer, San Pedro, CA (US); Rebecca Rajfer, Pittsburgh, PA (US)

(73) Assignee: K.L.R.M., LLC, San Pedro, CA (US)

( * ) Notice: Subject to any disclaimer, the term of this patent is extended or adjusted under 35 U.S.C. 154(b) by 0 days.

(21) Appl. No.: 15/719,783

(22) Filed: Sep. 29, 2017

(65) Prior Publication Data
US 2018/0104300 A1    Apr. 19, 2018

Related U.S. Application Data

(60) Provisional application No. 62/511,601, filed on May 26, 2017, provisional application No. 62/401,629, filed on Sep. 29, 2016.

(51) Int. Cl.
| | |
|---|---|
| A61K 36/906 | (2006.01) |
| A61P 19/10 | (2006.01) |
| A61K 31/198 | (2006.01) |
| A61K 36/77 | (2006.01) |
| A61K 36/9068 | (2006.01) |
| A61K 36/185 | (2006.01) |

(52) U.S. Cl.
CPC .......... *A61K 36/906* (2013.01); *A61K 31/198* (2013.01); *A61K 36/185* (2013.01); *A61K 36/77* (2013.01); *A61K 36/9068* (2013.01); *A61P 19/10* (2018.01)

(58) Field of Classification Search
None
See application file for complete search history.

(56) References Cited

U.S. PATENT DOCUMENTS

| | | |
|---|---|---|
| 2005/0234019 A1 | 10/2005 | Juturu et al. |
| 2007/0243132 A1 | 10/2007 | Russell-Jones et al. |
| 2012/0121740 A1 | 5/2012 | Rajfer |

OTHER PUBLICATIONS

Rajfer, et al., Enhancement of fracture healing in the rat, modulated by compounds that stimulate inducible nitric oxide synthase, Bone & Joint Research, vol. 6, No. 2, Feb. 2, 2017.

*Primary Examiner* — Susan Hoffman
(74) *Attorney, Agent, or Firm* — Welsh Flaxman & Gitler LLC

(57) ABSTRACT

A composition for enhancing treatment of orthopedic ailments stimulates iNOS and enhances treatment of orthopedic ailments when a pharmaceutically effective amount is administered over a sufficient period of time. The composition comprises ginger, *Muira puama*, *Paullinia cupana*, and at least one of the group consisting of L-arginine and L-citrulline.

11 Claims, 32 Drawing Sheets

1  NO IS MADE FROM L-ARGININE BY THE NOS ENZYME : SO INCREASE NOS

2  NO STIMULATES sGC ENZYME TO   CONVERT GTP TO cGMP : SO⇑sGC

3  PDE INHIBITORS : CAN INCREASE cGMP

US 10,426,812 B2

COMPOSITIONS AND METHODS FOR THE TREATMENT OF ORTHOPEDIC AILMENTS

CROSS REFERENCE TO RELATED APPLICATION

This application claims the benefit of U.S. Provisional Patent Application Ser. No. 62/401,629, entitled "COMPOSITIONS AND METHODS FOR FACILITATING HEALING OF BONE FRACTURE," filed Sep. 29, 2016 and this application claims the benefit of U.S. Provisional Patent Application Ser. No. 62/511,601, entitled "METHOD AND COMPOSITION FOR TREATMENT AND PREVENTION OF OSTEOPOROSIS," filed May 26, 2017.

BACKGROUND OF THE INVENTION

1. Field of the Invention

The present invention relates to compositions and methods for the treatment of orthopedic ailments. In accordance with one embodiment, the present invention relates to compositions and methods for treating fractured bone and/or increasing the rate of healing thereof. In accordance with such an embodiment, a nutraceutical composition that stimulates inducible nitric oxide synthase (iNOS) enhances bone fracture healing, as demonstrated by biomechanical properties. Use of the nutraceutical composition promptly after bone fracture enhances fracture healing. Further, the present invention relates to compositions, dosage forms, and methods for treating, inhibiting the onset, and/or slowing the rate of development of osteoporosis. In particular, the present invention relates to nutraceutical compositions, dosage forms, and methods for the treatment and/or prevention of osteoporosis via the up-regulation of iNOS.

2. Description of the Related Art

Bone fractures can be caused by force or pressure on a limb that exceeds the strength of the bone (e.g., flexural, torque and/or compression forces). Open or compound fractures occur when broken bone penetrates the skin, whereas in closed fractures, the skin remains intact. Fractures can be crosswise, lengthwise, and/or bones can be broken in multiple places. In addition to physical trauma, pathologic fracture of bones can be caused by disease, such as osteoporosis or bone cancer. Regardless of cause, the significant pain and dysfunction associated with bone fracture is often a life altering experience, aggravated by the long time required for bones to heal sufficiently to function normally. There has been a long felt need for medications and methods of treatment that expedite fracture healing.

Fracture healing results from a complex and sequential cascade of cellular events that restore bone to its pre-fracture condition. The space between the two ends of the fracture fill with a hematoma that is rich in mesenchymal cells and cytokines, which represents the soft callus that eventually undergoes an inflammatory phase followed by a reparative and then a remodeling phase.

Although the exact regulatory mechanisms for these phases are yet to be fully understood, neo-vascularity as well as osteoblast recruitment at the callus site appears to play a key role for successful healing.

With regard to osteoporosis, osteoporosis is a medical condition resulting in the loss of bone mass that results in the deterioration of bone architecture and an increase in the risk of fracture. Osteoporosis may occur primarily or secondarily as a result of another medical condition. Osteoporosis commonly affects both men and women age 50 years and older, although secondary osteoporosis can affect a person at any age. While there are various ways in which to treat osteoporosis there remains a need for a more simple, reliable and cost-effective way to treat those afflicted with osteoporosis.

The science behind the use of dietary supplements to treat diseases has increased over the past several decades. This includes the use of natural foods or products in combination with specific compounds. However, the biological and biochemical roles of these natural products are still being elucidated so that significant unpredictability remains for even small changes in formulations and/or depending on varying patient specific factors.

Arginine and other amino acids have been known for decades to play important roles in biological function of humans and animals in general. Ginger and other herbs are often combined in foods. A combination of rosemary with other ingredients (e.g., curcumin and quercetin) is taught in U.S. Patent Application Publication No. 2002/0051826, to Darland et al., for use in treating inflammation-related diseases. In addition to those main ingredients, Darland also suggests optionally using limonene, which can come from D-limonene or hesperidin, or the use of between 180 mg and 220 mg of ginger; the formulation can optionally include 180 mg to 220 mg of citrulline and other vitamins. Such reports suggest the safety of ingredients such as ginger, citrulline and arginine as long-term dietary supplements. While complex formulations such as those disclosed in the prior art are indicated to have general health benefits, there is a need for increased testing of specific formulations and determination of their impact, both positive and negative, on different aspects of health.

Thus, there remains substantial unpredictability in the benefits and detriments of natural herbs, with a wide range of conflicting and unreliable teachings, many based on anecdotal reports that cannot be reliably reproduced. In order to make a medical treatment recommendation, one of ordinary skill in the art of Western medical research requires data from studies that used accepted scientific methods. Such scientific methods include controls (e.g., placebo or baseline formulations), independent objective analysis, patient histories and patient monitoring before, during and after each study. Where possible, scientific methods should include double blind clinical trials and uniform compositions with reliable and consistent ingredients and analyses. Otherwise, the data and/or conclusions are subject to criticism as subjective, anecdotal, and/or wrong based on properly conducted studies, for example, studies of the type accepted by the U.S. Food and Drug Agency (US FDA), which may include an IRB protocol (Institutional Review Board protocol submitted to and approved by other scientists).

It is preferred to have study results that can be relied upon by clinicians trained in modern medicine and science. While it is desirable to use natural products that have well-established safety as foods in place of synthetic chemical pharmaceutical formulations, such use must be based on sufficient studies to justify replacing or supplementing medicines that have met regulatory and scientific scrutiny. The present inventors were challenged by the problems of finding compositions and methods for treatment and inhibition of osteoporosis that are practical for long-term routine administration (while avoiding side effects of existing formulations), enable treatment of and prevention of osteoporosis in patients that cannot utilize prior osteoporosis treatments, and/or provide new practical and cost-effective compositions to prevent as well as treat osteoporosis.

SUMMARY OF THE INVENTION

It is, therefore, an object of the present invention to provide a composition for enhancing treatment of orthopedic ailments, wherein administration of a pharmaceutically effective amount of the composition over a sufficient period of time stimulates iNOS and enhances the treatment of orthopedic ailments.

It is also an object of the present invention to provide a composition for enhancing treatment of orthopedic ailments wherein the composition comprises ginger or a ginger derivative, *Muira puama, Paullinia cupana*, and at least one of the groups consisting of L-arginine and L-citrulline.

It is another object of the present invention to provide a composition for enhancing treatment of orthopedic ailments wherein the composition comprises 250 mg to 2 g ginger or ginger derivative.

It is a further object of the present invention to provide a composition for enhancing treatment of orthopedic ailments wherein the ginger derivative is derived from *Zingiber officinale* roscoe or from rhizomes of *Zingiber officinale* roscoe.

It is also an object of the present invention to provide a composition for enhancing treatment of orthopedic ailments wherein the ginger or ginger derivative is selected from the group consisting of fresh, partially dried ginger, dried ginger, 6-gingerol.

It is another object of the present invention to provide a composition for enhancing treatment of orthopedic ailments including 10 mg to 3 g of L-arginine, L-citrulline, or a mixture of L-arginine and L-citrulline.

It is a further object of the present invention to provide a composition for enhancing treatment of orthopedic ailments including 10 mg to 2 g of L-arginine, L-citrulline, or a mixture of L-arginine and L-citrulline.

It is also an object of the present invention to provide a composition for enhancing treatment of orthopedic ailments including 100 mg to 3 g of *Muira puama*.

It is another object of the present invention to provide a composition for enhancing treatment of orthopedic ailments including 500 mg to 1.5 g of *Muira puama*.

It is a further object of the present invention to provide a composition for enhancing treatment of orthopedic ailments including at least 250 mg of *Paullinia cupana*.

It is also an object of the present invention to provide a composition for enhancing treatment of orthopedic ailments including 500 mg of *Paullinia cupana*.

It is another object of the present invention to provide a composition for enhancing treatment of orthopedic ailments including 250 mg to 2 g of ginger or ginger derivative, 250 mg to 2 g of L-arginine, L-citrulline, or mixture of L-arginine and L-citrulline, 500 mg to 1.5 g of *Muira puama*, and 500 mg of *Paullinia cupana*.

It is a further object of the present invention to provide a composition for enhancing treatment of orthopedic ailments wherein administration of the pharmaceutically effective amount of the composition over the sufficient period of time will increase the rate of bone fracture healing.

It is also an object of the present invention to provide a composition for enhancing treatment of orthopedic ailments wherein administration of the pharmaceutically effective amount of the composition over the sufficient period of time is effective in treatment of osteoporosis.

It is another object of the present invention to provide a composition for enhancing treatment of orthopedic ailments wherein the composition is in an oral dosage form comprising a tablet, capsule, lozenge or suspension.

It is a further object of the present invention to provide a method for enhancing treatment of orthopedic ailments comprising administering a pharmaceutically effective amount of a composition over a sufficient period of time to stimulate iNOS and enhance treatment of orthopedic ailments.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
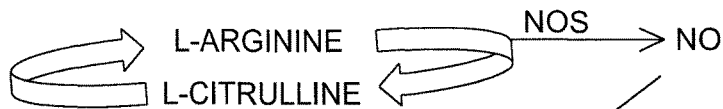
FIG. 1 is a schematic representation explaining the three mechanisms for the up-regulation of the nitric oxide-cGMP pathway.
Figure 1:
Figure 1:
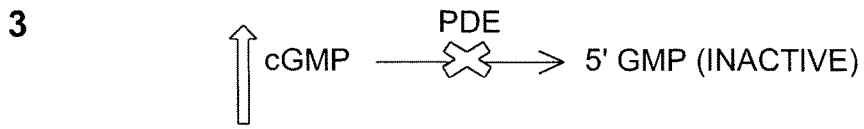

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

The present invention provides compositions and methods for the treatment of orthopedic ailments. In particular, the present invention provides a nutraceutical composition for treating fractured bone and/or increasing the rate of healing thereof. The present invention also provides a nutraceutical composition for treating osteoporosis. The nutraceutical composition (which is referenced herein and in various figures as COMB-4) comprises effective amounts of ginger or a ginger derivative selected from the group consisting of fresh, partially dried vegetable ginger, dried vegetable ginger, 6-gingerol and mixtures thereof; at least one of the group consisting of arginine and citrulline (preferably, L-arginine, L-citrulline, or a combination of L-arginine and L-citrulline); *Muira puama*; and *Paullinia cupana* (guarana).

Ginger is a complex natural composition having numerous purported properties when used alone and/or in combination with other compounds. For example, traditional Chinese medicines have used or included ginger in compositions to treat or prevent various maladies based on a variety of metaphysical reasons. Over the past century, scientific methods have shown that many traditional Chinese medicines do not produce the purported effects and/or may even make the target maladies worse. Nevertheless, some traditional Chinese medicines have been found to contain active agents that may be of medical use, even if not effective or safe for the use purported by traditional Chinese medicine. The complexity of ginger and its myriad properties is reflected by certain constituent compounds which have the following structure:

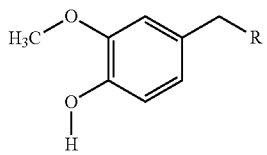

wherein, for example, in 6-gingerol the R sidechain of the vanillyl function group (i.e., 4-hydroxy-3-methoxyphenyl group) is:

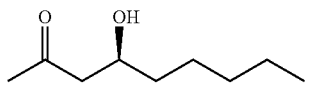

Thus, 6-gingerol (also called gingerol) is (S)-5-hydroxy-1-(4-hydroxy-3-methoxyphenyl)-3-decanone and has the following structure:

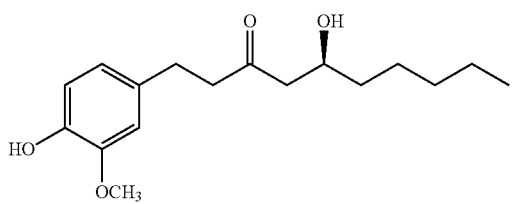

Since ginger contains multiple compounds, of varying complexity and chemical activity, there are conflicting teachings in the art about the biological activity of compounds that might be useful in inducing nitric oxide (NO) production or otherwise having a potential role in treatment. Further, there remains considerable unpredictability about how to understand, much less control, the relevant metabolic pathways. However, the applicant has discovered that ginger, when combined with *Muira puama*, *Paullinia cupana* (guarana), and at least one of the group consisting of arginine and citrulline (preferably, L-arginine, L-citrulline, or a combination of L-arginine and L-citrulline) can be effectively used to treat orthopedic ailments.

An oral dosage form of the nutraceutical composition in accordance with the present invention is selected from the group consisting of a tablet, capsule, lozenge, powder or suspension comprising the foregoing ingredients. Preferred suspensions are aqueous and/or alcohol (ethanol) based.

The raw materials and ingredient matter may be dried, for example by freeze-drying or vacuum drying, before compounding into oral dosage forms. Individual dosage forms may comprise compressed tablets, capsules, lozenges or may be provided in sachets. Suspension formulations may be provided. Ginger, ginger root extract, L-arginine, L citrulline, *Muira puama* and *Paullinia cupana* are all separately commercially available, with preferred sources and analyses provided infra. Preferably, the ingredients are combined and encapsulated in gelatin capsules, but other dosage forms are anticipated that will produce equivalent results.

Flavorings or taste masking agents may be employed. Tablets or other dosage forms may include diluents (e.g., lactose), disintegrants (e.g., cross carmelose sodium), or binders (e.g., polyvinylpyrollidone). Lubricants for example magnesium stearate, or other conventional excipients may be employed (e.g., silicas, carbohydrates, etc.). Film-coated tablets may be provided.

The active ingredients of compositions of the present invention are combined using well known and standard processes and agents. Preferably, a gelatin capsule contains the combined ingredients in powder form. Standard ingredients in powder formulations are used for preparing and compounding preferred exemplary formulations of the present inventions. For example, carrier silica (e.g., Spernat 50S® from Evonik Degusa Industries of Parsippany, N.J., USA) can be used to convert liquids into free flowing powders and/or can be used to enhance flowability and shelf life of powdered products (especially powders prone to caking). Magnesium stearate (octadecanoic acid, magnesium salt, e.g., LIGAMED from Peter Greven of the Netherlands) can be used as a diluent with lubricating properties helpful to prevent the composition and its ingredients from sticking to manufacturing equipment, and can also serve as a binding agent. The ingredients, in powder form, are inspected, weighed, blended and encapsulated in gelatin capsules. The blending process includes standard screening, blending and metal detection at standard temperatures and in a sterile environment at least sufficient for food supplements.

Sources of active ingredients may include:
EXEMPLARY ACTIVE INGREDIENT SOURCES
Ginger
SUPPLIER 1. SOLARAY GINGER Root Extract
Ginger root—250 mg (5% gingerols)
Gingerols—12.5 mg/5%
Other ingredients: Magnesium Stearate, Croscamellose Sodium
Park City, Utah
www.Solaray.com
SUPPLIER 2. NATURE'S ANSWER, INC. Ginger Rhizome Extract
Ginger Rhizome Extract—125 mg standardized for 5% gingerols+shogoals)
Other ingredients: Vegetable Cellulose, Rice Flour, Di-Calcium Phosphate, Calcium Silicate
Hauppauge, N.Y. 11788-3943
http://www.naturesanswer.com/
SUPPLIER 3. SOLGAR GINGER Root Extract
Ginger Root Extract—300 mg (5% ginger phenols)
Raw Ginger Powder—150 mg C-ascorbic acid, beta-carotene, magnesium stearate, monocrystalline cellulose
Veronica, N.J.
SOLGAR GINGER Powder
Ginger powder—500 mg
Root Ginger Extract 4:1-5 mg
L-Citrulline
SOURCE NATURALS L-Citrulline Free-Form Amino Acid Supplement:
L-Citrulline 2 g
Other Ingredients: gelatin (capsule), microcrystalline cellulose, colloidal silicon dioxide, and magnesium stearate.
Source Naturals, Inc.
P.O. Box 2118
Santa Cruz, Calif. 95062
http://www.sourcenaturals.com/
L-Arginine
THE VITAMIN SHOPPE L-ARGININE
L-Arginine—500 mg
Vitamin B6 10 mg
Other Ingredients: gelatin, rice flour, magnesium stearate
*Muira Puama*
SUPPLIER 1. SOLARAY *Muira puama* Ptychopetalum Olacoides Dietary Supplement:
*Muira puama* Ptychopetalum Olacoides (root)—600 mg
Other Ingredients: Gelatin Capsule, and Cellulose.
Manufactured by Nutraceutical Corp.
Park City, Utah 84060
http://www.solaray.com
SUPPLIER 2. NATURE'S ANSWER *Muira puama* Organic Alcohol Extract:
*Muira puama* Root Extract (1:1)—2000 mg
Other Ingredients: Purified Water, Vegetable Glycerin, 12-15% Certified
Organic Alcohol
*Paullinia Cupana* (Guarana)
SOURCE NATURALS Guarana Energizer Dietary Supplement:
Guarana Seed Extract (22% caffeine)—900 mg
Other Ingredients: Microcrystalline cellulose, dibasic calcium phosphate, stearic acid, modified cellulose gum, and colloidal silicon dioxide.
Source Naturals, Inc.
P.O. Box 2118
Santa Cruz, Calif. 95062
http://www.sourcenaturals.com/

Since certain preferred formulations of the present nutraceutical composition comprise compounds found in foods or extracted from foods, they may be referred to as "nutraceuticals." While nutraceutical compositions have traditionally been found in a medicinal format, such as capsules or tablets, an increasing number of foods have been fortified with nutraceuticals. Analogs and/or homologs of ginger constituents in combination with *Muira puama, Paullinia cupana* (guarana), and L-arginine and/or L-citrulline are used in accordance with the present invention to promote iNOS sufficient to ameliorate, stop or reverse fibrotic events associated with osteoporosis, or enhance bone healing associated with fractures. The present nutraceutical composition can therefore be administered in a wide variety of ways and forms matching the lifestyle and dietary preferences of the users, as once or twice a day dietary supplements, mixed into foods or "smoothies," etc.

Significant medical advancements have resulted from the use of natural products in either their native form, as extracts, or concentrates. For example, acetylsalicylic acid (or Aspirin) was derived from Willow trees. Likewise, the anticancer drug Taxol was isolated from the Western Yew tree. As a result natural products have been used for treating various diseases for many years. Many natural products have been purported to increase sexual potency, treat sexual problems, or act as aphrodisiacs.

There is, however, a great deal of unpredictability due to the complexity of biological systems, variations in plants and their derivatives based on the soil and climate, as well as interactions with other compounds, etc. The applicant has found that through the use of the present nutraceutical composition the symptoms of osteoporosis appear to be reduced beyond the predicted bioavailability of the nutraceutical composition of the present inventions. Similarly, applicant has found that the nutraceutical composition of present invention improves the healing of bone fracture.

"Effective amount" as used in the present disclosure is intended to mean that a dosage form of the nutraceutical composition contains an amount of each ingredient sufficient when administered to a human patient for a sufficient period of time to produce a beneficial orthopedic effect, for example, in treating fractured bone and/or increasing the rate of healing thereof, or in treating, inhibiting the onset and/or slowing the rate of development of osteoporosis. The beneficial effect includes, in the context of treating fractured bone, at least one of increase in bone mineral density (BMD), acceleration of fracture healing, healing of malunion or nonunion (whether primarily or adjunctively), and more rapid bony in-growth or on-growth on implants that require bone growth for optimal function. The beneficial effect includes, in the context of osteoporosis, at least one of increase in bone mineral density (BMD), acceleration of fracture healing, healing of malunion or nonunion (whether primarily or adjunctively), and more rapid bony in-growth or on-growth on implants that require bone growth for optimal function.

"Individual Dosage" as used herein means the amount of the nutraceutical composition in a single dose of the nutraceutical composition administered to a human patient as part of a dosing regimen.

"Total Daily Dosage" as used herein means the cumulative amount of the nutraceutical composition administered to a human patient over the course of a day whether the nutraceutical composition is administered once a day or multiple times a day as part of a dosing regimen.

"About" as used herein means refers to a range of values+/−10% of a specified value.

Compositions and Methods for Facilitating Healing of Bone Fracture

Inducible nitric oxide synthase (iNOS) has been shown to play a major role in the process of fracture healing. The present invention considers the effects of upregulators of iNOS on fracture healing. In particular, the effects of tadalafil (a phosphodiesterase (PDE) inhibitor) and the nutraceutical composition COMB-4 of the present invention (consisting of L-citrulline, *Paullinia cupana*, ginger and *Muira puama*), given either singly or in combination, on bone fracture healing are considered. Experiments in a rat model that is considered an excellent basis for human applicability confirm the benefits of administration of the nutraceutical composition of the present invention on bone fracture healing. For example, the formulations of the nutraceutical composition of the present invention were given daily to rats that had unilateral open fractures, and, after sacrifice early (day 14) and late (day 42), fracture healing was analyzed. It was surprisingly discovered that the nutraceutical composition of the present invention caused a significant enhancement of bone fracture healing. In contrast, tadalafil, despite its known iNOS activity, did not demonstrate significant improvement in fracture healing. While a higher dose of tadalafil might be used, the practical limits of dose tolerability would be challenged. In view of the well-known side effects of tadalafil (and other PDE inhibitors), the nutraceutical composition of the present invention has surprising benefits, including that it is well tolerated at even higher dosages than used in the study, and is formed of ingredients that have been widely used without adverse health effects. The following experimental details demonstrate a preferred non-limiting example of use of nutraceutical composition of the present invention, alone, or in combination with a PDE inhibitor, to improve bone fracture healing.

In accordance with a preferred embodiment, the total daily dosage of the nutraceutical composition is
- up to about 3 g (preferably about 250 mg to about 2 g) ginger or ginger derivative,
- about 10 mg to about 2 g (preferably about 400 mg to about 2 g) of a L-citrulline, L-arginine or a combination of L-arginine and L-citrulline,
- about 100 mg to about 3 g (preferably about 500 mg to about 1.5 g) *Muira puama*, and
- at least about 125 mg (preferably about 500 mg) *Paullinia cupana* (guarana).

A specific individual dosage forming the basis for the test results presented herein, where the nutraceutical composition is taken only once a day, includes
- about 500 mg ginger or ginger derivative,
- about 1,600 mg L-citrulline,
- about 500 mg *Muira puama*, and
- about 500 mg *Paullinia cupana*.

While a daily administration of the nutraceutical composition of the present invention was used during testing, it is appreciated the nutraceutical composition may be administered multiple times a day and the individual dosages would therefore be adjusted so as to not exceed the preferred total daily dosage as outlined above. Whether the nutraceutical composition is administered once a day or multiple times throughout the day, the nutraceutical composition is administered for a sufficient period of time to treat fractured bone and/or increase the rate of healing thereof. In addition, *Paullinia cupana* formulations used in making compositions of the present inventions may optionally include caffeine.

The nutraceutical composition may include optional pharmaceutically acceptable excipients, fillers, binders, and colorants, and can be packaged in standard gelatin capsules or formed into solid tablets, taken in particulate form, or mixed into and/or suspended in solution.

The present nutraceutical composition reflects the ability of a combination of ginger, *Muira puama, Paullinia cupana* (guarana), and L-citrulline and/or L-arginine to treat fractured bone and/or increase the rate of healing thereof. The nutraceutical composition may be taken for an indefinite period to sustain the beneficial effects.

Considering now the mechanisms by which the present composition works, nitric oxide (NO) is known to be an important signaling molecule in many physiological systems. Nitric oxide is also known as a potent anti-oxidant and anti-apoptotic molecule (meaning that it fights cellular death). Still further, nitric oxide is known to mediate pro-survival effects of 17 beta estradiol in osteoblasts via sGC (Soluble Guanylyl Cyclase) activation. Marathe et al. Pro-Survival effects of 17 beta-estradiol on osteocytes are mediated by nitric oxide/cGMP via differential actions of cGMP-dependent protein kinases 1 and 11. *J Biol Chem* 2012; 287(2):978-88) Treatment with a combination of ginger, L-citrulline, *Muira puama* and *Paullinia cupana* can reverse the progression of corporal smooth muscle loss, fibrosis and veno-occlusive dysfunction in the aging rat. *Andrology (Los Angel)*. 2015 June; 4(1). pii: 132. Epub 2015 May 25. It is further recognized that mechanical stimulation induces osteoblast proliferation via the nitric oxide, cGMP (Cyclic Guanosine MonoPhosphate), and PKG (Protein Kinase G) pathway as discussed below in greater detail. Rajfer R et al. Enhancement of fracture healing in the rat, modulated by compounds that stimulate inducible nitric oxide synthase: Acceleration of fracture healing via inducible nitric oxide synthase. BJR 2017 February; 6(2):90-97. Nitric oxide itself can either work directly inside the mitochondria to quench or stop oxidative stress, or the nitric oxide can convert a molecule called GTP (Guanosine TriPhosphate) to cGMP. The present nutraceutical composition upregulates the nitric oxide-cGMP pathway to enhance osteoblastic function/proliferation for the purpose of treating fractured bone and/or increasing the rate of healing thereof.

Neovascularity and osteoblastic recruitment are known effects of nitric oxide, which appears to be involved in the fracture healing process. Hikiji H, Shin W S, Oida S, et al. Direct action of nitric oxide on osteoblastic differentiation. *FEBS Lett* 1997; 410:238-242. Baldik Y, Talu U, Altinel L, et al. Bone healing regulated by nitric oxide: an experimental study in rats. *Clin Orthop Relat Res* 2002:343-352.

Nitric oxide is produced by one of three isoforms of nitric oxide synthase (NOS) depending on tissue location and physiological function. Bredt D S. Endogenous nitric oxide synthesis: biological functions and pathophysiology. *Free Radic Res* 1999; 31:577-596. Förstermann U, Gath I, Schwarz P, et al. Isoforms of nitric oxide synthase. Properties, cellular distribution and expressional control. Biochem Pharmacol 1995; 50:1321-1332. While all three of these NOS isoforms are involved in the fracture healing process, inducible NOS (iNOS) appears to be the primary isoform involved in the stimulation of osteoblasts by nitric oxide. Corbett S A, Hukkanen M, Batten J, et al. Nitric oxide in fracture repair. Differential localisation, expression and activity of nitric oxide synthases. *J Bone Joint Surg [Br]* 1999; 81-B:531-537. Diwan A D, Wang M X, Jang D, et al. Nitric oxide modulates fracture healing. J Bone Miner Res 2000; 15:342-351. Zhu W, Murrell G A, Lin J, et al. Localization of nitric oxide synthases during fracture healing. *J Bone Miner Res* 2002; 17:1470-1477. Hukkanen M, Hughes F J, Buttery L D, et al. Cytokine-stimulated expression of inducible nitric oxide synthase by mouse, rat, and human osteoblast-like cells and its functional role in osteoblast metabolic activity. Endocrinology 1995; 136:5445-5453. Wimalawansa S J. Nitric oxide and bone. *Ann N Y Acad Sci* 2010; 1192:391-403. Furthermore, when the iNOS gene is selectively deleted, fracture healing is impaired. This can be reversed by treatment with the iNOS gene. Baldik Y, Diwan A D, Appleyard R C, et al. Deletion of iNOS gene impairs mouse fracture healing. Bone 2005; 37:32-36.

The effects of nitric oxide are normally mediated via its second messenger, cGMP, which is regulated by intracellular phosphodiesterase (PDE). Katsuki S, Arnold W, Mittal C, Murad F. Stimulation of guanylate cyclase by sodium nitroprusside, nitroglycerin and nitric oxide in various tissue preparations and comparison to the effects of sodium azide and hydroxylamine. J Cyclic Nucleotide Res 1977; 3:23-35. Arnold W P, Mittal C K, Katsuki S, Murad F. Nitric oxide activates guanylate cyclase and increases guanosine 3':5'-cyclic monophosphate levels in various tissue preparations. *Proc Natl Acad Sci USA* 1977; 74:3203-3207. Weiss B.

Differential activation and inhibition of the multiple forms of cyclic nucleotide phosphodiesterase. *Adv Cyclic Nucleotide Res* 1975; 5:195-211. Inhibitors of PDE, such as tadalafil, are known to increase intracellular cGMP and have been shown to accelerate early fracture healing in mice. Recently, Ferrini et al. reported that a combination of the four herbal compounds, L-citrulline, ginger, *Paullinia cupana*, and *Muira puama* (COMB-4), originally conceived as an anti-fibrotic compound, appeared in an in vivo study to produce a marked stimulation of the iNOS enzyme in rats. Histing T, Marciniak K, Scheuer C, et al. Sildenafil accelerates fracture healing in mice. *J Orthop Res* 2011; 29:867-873. Toğral G, Arikan M, Korkusuz P, et al. Positive effect of tadalafil, a phosphodiesterase-5 inhibitor, on fracture healing in rat femur. *Eklem Hastalik Cerrahisi* 2015; 26:137-144. Ferrini M G, Hlaing S M, Chan A, Artaza J N. Treatment with a combination of ginger, L-citrulline, *Muira puama* and *Paullinia cupana* can reverse the progression of corporal smooth muscle loss, fibrosis and veno-occlusive dysfunction in the aging rat. *Andrology (Los Angeles)* 2015; 4:132.

With the foregoing in mind, the present nutraceutical composition composed of (1) ginger or ginger derivative, (2) L-citrulline, L-arginine, or mixture of L-arginine and L-citrulline, (3) *Muira puama*, and (4) *Paullinia cupana* is useful in treating fractured bone and/or increasing the rate of healing thereof. This nutraceutical composition results in an upregulation of the nitric oxide-cGMP pathway which results in the treatment of fractured bone and/or increases in the rate of healing thereof treatment.

As shown in FIG. 1, there are three mechanisms for the upregulation of the nitric oxide-cGMP pathway. In accordance with the first mechanism, nitric oxide is made from L-arginine via the action of an enzyme called nitric oxide synthase (NOS). NOS is an enzyme that converts L-arginine to nitric oxide. When L-arginine is used in making nitric oxide as shown above, L-arginine is converted to L-citrulline. The body is very smart, and the cells will then take L-citrulline and reconvert it back to L-arginine via another enzymatic pathway.

In accordance with a second mechanism, it is appreciated that once nitric oxide is formed, it exists as a gas that only lasts a few seconds, if any. But it is so potent, it will stimulate another enzyme called soluble guanylyl cyclase (sGC). sGC is the enzyme that converts the GTP to the second messenger in the nitric oxide-cGMP pathway, cyclic GMP. So again, theoretically, if one upregulates sGC, a more efficient production of cGMP is achieved.

Finally, and in accordance with the third mechanism, PDE inhibitors are used to prevent the breakdown of cGMP to 5'GMP. When cGMP, or any of the cyclic nucleotides like cyclic AMP (Adenosine Monophosphate), is produced the body has enzymes (that is, PDE5) to break it down in order to moderate or regulate the physiological process. The cGMP is broken down within the cell to produce 5'GMP, which is an inactive compound. If the PDE5 enzyme is blocked, the levels of cGMP are elevated because cGMP is not being degraded in its normal way.

As explained above, nitric oxide is produced in the body via three different mechanisms. The mechanism contemplated in accordance with the present invention involves the utilization of the enzyme iNOS, which is produced within the cells. iNOS is an enzyme that is only normally located in the cells that fight infection. In accordance with the present invention, it has been found that once people start aging, iNOS begins to be produced within the cells.

Figure 2:
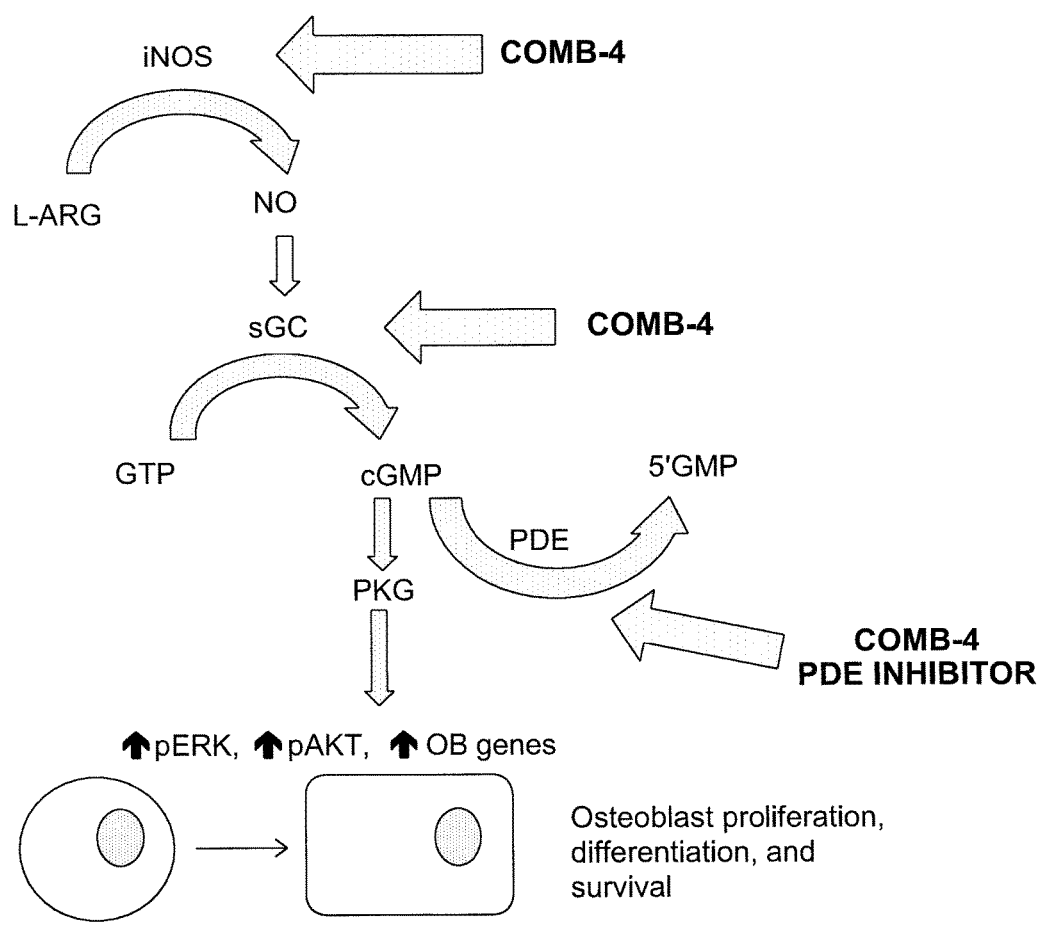
FIG. 2 is a schematic representation of the biological pathways upon which the present nutraceutical composition acts in order to up-regulate the nitric oxide-cGMP pathway for the purpose of treating fractures.

With reference to FIG. 2, the present invention focuses upon osteoblasts, which are cells intimately involved in bone metabolism. Osteoblasts, among other roles that are not fully understood, secrete the matrix for bone formation. The nutraceutical composition of the present invention increases the nitric oxide-cGMP pathway by increasing nitric oxide production and decreasing the conversion of cGMP to 5'GMP. This results in an increase in osteoblast proliferation, differentiation and survival by increasing pERK (Phosphorylated Extracellular Signal-Regulated Kinase), pAKT (Phosphorylated AKT (Protein kinase B), and OB genes (Obese Genes).

As briefly mentioned above, efficacy of the present nutraceutical composition was tested. Fifty-eight male Sprague-Dawley rats (10 weeks old, body weight (BW): 344±11 g) were used for this study, which was approved by the Institutional Animal Care and Use Committee of the Charles R. Drew University of Medicine and Science. The rats were housed for one week prior to experimental procedures to permit acclimatization and then randomly assigned to three groups. The control group (n=19 rats) received 0.2 ml of vehicle composed of 10% dimethyl sulfoxide (DMSO), peanut butter and water by retro-lingual administration. The tadalafil group (n=20 rats) was given a daily oral dose of 2.0 mg/kg body weight (BW) of the PDE5 inhibitor, tadalafil (Eli Lilly, Indianapolis, Ind.), mixed with vehicle. This dose has been shown to be equivalent to a 20 mg/day daily dose in humans.

The COMB-4 group (Naturex, Hackensack, N.J.; n=19 rats), that is, the group receiving the nutraceutical composition in accordance with the present invention, received a combination of *Muira puama* (45 mg/kg body weight BW), *Paullinia cupana* (45 mg/kg BW), ginger (45 mg/kg BW) and L-citrulline (133 mg/kg BW) dissolved in vehicle. The appropriate rat dose of each of the four components of COMB-4 was calculated based on the equivalent recommended human daily dose as previously reported. See International Patent Publication Number WO 2012/067745 A 1 for more details on the ingredients in COMB-4, ranges of ingredients, and the beneficial effects thereof in treating Erectile Dysfunction and cardiovascular disease.

All animals received the vehicle only for the three days prior to surgery to get the animals adapted to the taste, and began receiving either their respectively assigned control or experimental daily dose of tadalafil or COMB-4 on the same day right after the fracture (day 0).

All surgeries were performed by one orthopedic surgeon who was blinded to the rats' experimental assignment. Anesthesia was induced with 3% isoflurane and maintained with 2.5% isoflurane throughout the surgery. All rats received subcutaneous injections of buprenorphine 0.05 mg/kg body weight for pre- and postoperative pain control.

Each rat then underwent a unilateral femur fracture with internal fixation. Briefly, after shaving the skin, the rat was placed in the supine position and a longitudinal incision 1.5 cm long centered over the superior patella was made just medial to the midline. The underlying fascia was incised at the medial patellar tendon border and the patella was dislocated laterally. The trochlea was opened with a 1.0 mm drill bit and the intramedullary canal and greater trochanter were reamed with a 21-3 gauge hypodermic needle. The intramedullary canal was sequentially reamed with an 18-gauge needle, and the epicondyle was further opened with a 16-gauge needle. The femoral shaft was accessed by sweeping the vastus medialis laterally. A cat claw scissors (Petco, San Diego, Calif.) placed at the junction of the middle and distal one-third of the femoral shaft was used to make a transverse fracture. A randomizer table was used to determine laterality of the osteotomy. While maintaining control of both fracture fragments, a titanium compression intramedullary screw (RISystem, Davos, Switzerland) was applied in a retrograde manner while directly visualizing the fracture reduction. A small amount of compression was seen at the fracture site indicating the intramedullary screw obtained fixation proximally at the greater trochanter and the site was tested manually for any movement.

The fascia and skin were closed in two layers utilizing 4-0 Vicryl (Ethicon Inc., Somerville, N.J.) and VetBond skin glue (3M, St. Paul, Minn.). A small amount of triple antibiotic ointment (Actavis, Parsippany, N.J.) was applied to the skin. Range of motion at the hip and knee was performed to ensure there was no penetration of the screw proximally and that the patella was adequately tracking. Unprotected weight bearing was permitted immediately postoperatively, and on day 14, 5 rats from each group were euthanized using inhalational $CO_2$ and femora were harvested for qCT (quantitative computerized tomography) and histological evaluation. On day 42, fifteen (15) rats from each group were euthanized for qCT and histological evaluation. The remaining rats were euthanized for biomechanical testing.

Callus Development Analysis Via qCT

Mineral Content and Callus Volume. A quantitative determination of callus development at days 14 and 42 was obtained via quantitative computerized tomography (qCT: XCT 3000, Stratec, Pforzheim, Germany). The qCT was selected because it allows three-dimensional, quantitative evaluation of fracture healing, including callus development at the fracture site. Three parameters were quantified: cross-sectional transverse area, bone mineral content and bone density.

After removal of the intramedullary screw, a bony section 3 mm in length, which included the fracture in the middle, was analyzed using three consecutive transverse qCT scans of 1.1 mm in thickness and 0.1×0.1 mm in pixel size. Three images were obtained: one image for the bone fragment proximal to the fracture, one image for the fracture site itself and one image for the distal bone fragment. XCT Series software package (version 5.21, Stratec, Pforzheim, Germany) was used to calculate the mineral content, mineralized callus area and bone mineral density of each image.

Total mineral content and callus volume of the 3 mm segment were calculated by combining all three sections values. In order to assess progression of remodeling, higher density callus (>500 mg/cm3) was measured and separated from total callus (>299 mg/cm3). Mineral density greater than 850 mg/cm3 was considered cortical bone density and was eliminated from newly formed callus calculations.

Immunohistochemical Expression of iNOS. After qCT measurements, specimens were fixed in 4% p-formaldehyde and were decalcified in 10% formic acid for five days. Each femur was rinsed in phosphate-buffered saline, both epiphyses were removed and the shaft was cut longitudinally in two halves. Both halves were processed for paraffin embedding sections. Five-micrometer paraffin embedded sections were employed for immunostaining with polyclonal antibody against iNOS. Briefly, sections were deparaffinized through a series of xylene baths and rehydrated through graded alcohols.

Endogenous peroxidase activity was quenched with 0.3% hydrogen peroxide for 20 min and nonspecific binding was blocked with 10% normal goat serum for 40 min. Sections were incubated overnight at 4 degrees Celsius (C) with primary polyclonal antibody against iNOS (BO Pharmagen, dilution 1:250). Next, the sections were then incubated with biotinylated anti-Rabbit IgG, respectively, followed by ABC complex (Vector labs, Temecula, Calif.) and 3,3'diaminobenzidine (Sigma) slides were counterstained with a hematoxylin solution. Stained sections were dehydrated and then mounted with Permount. At least six pictures per section were taken with a Leica microscope at 20× magnification. Integrated optical density (100) per cell was determined using Image Pro 7.1 software (Media Cybernetics, Silver Spring, Mo., USA). After images were calibrated for background lighting, 100 results are proportional to the unweighted average optical density which is used to determine the concentration of immunoreactive antigen.

Each slide assayed had its corresponding negative control. In all cases, six non-overlapping fields were screened per tissue sections and at least three sections per animal were analyzed.

Biomechanical Evaluation. After euthanasia at day 42, each femur was harvested and both ends of the femur were embedded in blocks of polymethyl methacrylate (PMMA) after removal of the intramedullary screw. Only a 12 mm long segment of the bone, which included the fracture in the center, was exposed. The specimen was then secured onto a torsional testing apparatus mounted into an MTS bi-axial load frame (MTS mini-bionix 858, Minneapolis, Minn.). Torsion to failure was applied at a rate of 12 degrees/min.

Two parameters were derived from the torque-displacement curve for each specimen's load to failure test: torsional stiffness and maximum torque. Additionally, using the failure pattern, each specimen was classified into one of four biomechanical stages of fracture repair as described by White et al., (The four biomechanical stages of fracture repair, J Bone Joint Surg Am. 1977 March; 59(2):188-92.) Stage I fractures were rubbery, indicating only soft callus formation. Stages II through IV exhibited higher stiffness, indicating failure of bone with progressively higher mineralized tissue. Stage I and II fractures failed through the original fracture line. Stage III failure occurred partially through the original fracture line and partially through intact bone, while Stage IV failure occurred entirely through intact bone.

Statistical Analysis. Analysis of variance (ANOVA) was used to compare the outcome variables, including callus volume, bone mineral content, bone density, torsional stiffness and maximum torque at failure. The independent variables were day 14 and day 42 and treatment type (four categories including control). ANOVA was followed by Least Significant Difference (LSD) post-hoc tests to compare individual pairs of groups.

Non-parametric tests were used to compare the fracture repair stages among the four groups. For quantitative image analysis of the histological observations values were expressed as the mean±SEM. The normality distribution of the data was established using the Wilk-Shapiro test. Multiple comparisons were analyzed by a single factor analysis of variance followed by post hoc comparisons with the Tukey test according to GraphPad Prism (version 5.1) for Windows (GraphPad Software, San Diego Calif.). Differences were considered significant at $p<0.05$.

Results. Five rats (2 from 14 days and 3 from 42 days) were excluded from the study due to either an infection discovered at the fracture site (n=4) or a postoperative comminuted fracture (n=1).

Callus Development Analysis

Mineral Content and Callus Volume. All three groups demonstrated about a 50% increase in both the mineral content and mineralized callus volume at the osteotomy site at day 42 when compared to day 14 (see Table 1). However, at both these time points neither the tadalafil nor the COMB-4 group demonstrated statistical difference compared to the control group. While callus is relevant to the healing process, the fact no statistical difference was observed was considered not to have a bearing on the efficacy of COMB-4 in the treatment of bone fractures.

TABLE 1

Newly formed callus, total and hard callus, and newly formed hard callus at the osteotomy site at days 14 and 42 (mean ± S.D.)

Newly formed Total Callus ( >299 mg/cm$^3$)

| Group | Callus Volume (mm$^3$) | | Mineral Content (mg) | | Bone Density (mg/cm$^3$) | |
| --- | --- | --- | --- | --- | --- | --- |
| | Day 14 | Day 42 | Day 14 | Day 42 | Day 14 | Day 42 |
| Control | 44 ± 9.1 | 64.0 ± 18.1 | 19.7 ± 4.7 | 33.0 ± 10.2 | 445.8 ± 23.3 | 512.2 ± 16.2 |
| Tadalafil | 44.9 ± 11.7 | 66.3 ± 22.3 | 20.8 ± 6.3 | 34.1 ± 12.7 | 458.4 ± 29.2 | 510.0 ± 18.9 |
| COMB-4 | 37.3 ± 8.6 | 63.2 ± 9.6 | 16.4 ± 4.2 | 31.7 ± 5.6 | 438.4 ± 10.0 | 500.0 ± 17.9 |

Newly formed Total Callus ( >500 mg/cm$^3$)

| Group | Callus Volume (mm3) | | Mineral Content (mg) | | Bone Density (mg/cm$^3$) | |
| --- | --- | --- | --- | --- | --- | --- |
| | Day 14 | Day 42 | Day 14 | Day 42 | Day 14 | Day 42 |
| Control | 15.1 ± 4.3 | 35.7 ± 10.9 | 10.0 ± 2.8 | 24.6 ± 7.1 | 659.0 ± 9.0 | 693.2 ± 23.8 |
| Tadalafil | 16.4 ± 4.7 | 35.6 ± 12.6 | 11.0 ± 3.8 | 24.1 ± 8.3 | 665.0 ± 2.0 | 697.2 ± 12.4 |
| COMB-4 | 13.3 ± 3.0 | 33.4 ± 7.0 | 8.8 ± 1.9 | 22.8 ± 4.7 | 661.0 ± 10.0 | 683.7 ± 5.0 | n = 4 for Day 14 Control, Tadalafil, and Day 42 COMB4 groups.
n = 5 for Day 14 COMB-4 and Day 42 Control and Tadalafil groups.

Figure 3:
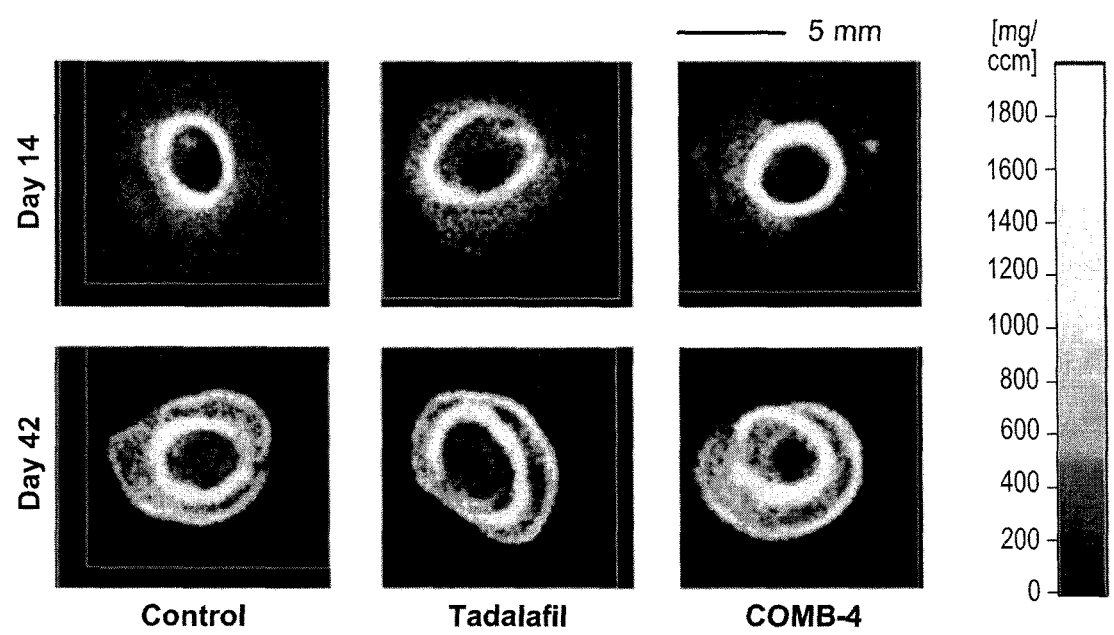
FIG. 3 shows representative qCT images of three (3) groups. The qCT images were taken at 1 mm below each fracture site to eliminate bone fragments overlap at the fracture level. Total mineral content and callus volume of a fracture were calculated by combining values of three sections, at the fracture site and 1 mm above and below. The right side bar indicates bone mineral density.
Figure 4:
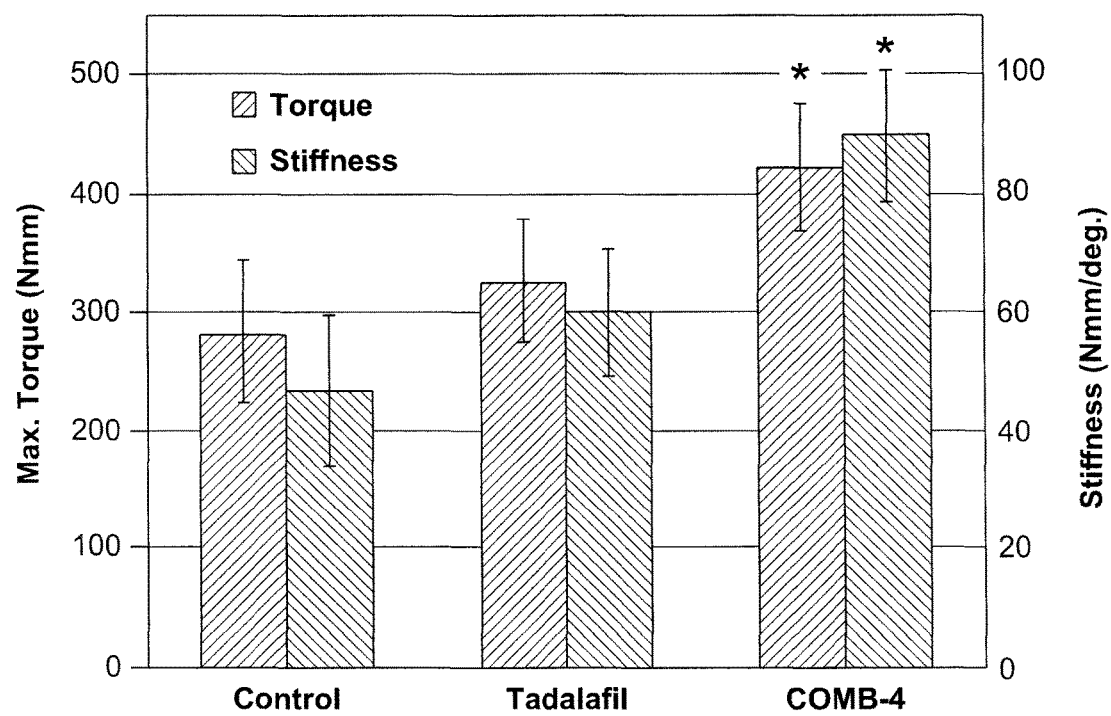
FIG. 4 shows maximum torque (strength) and stiffness of healing fracture at day 42. Results are expressed as mean±S.E.*$p<0.05$ compared to control group.

FIG. 3 shows representative CT images of the three groups at the two different time points.

Biomechanical Properties. At day 42, the mean values for all three biomechanical parameters (fracture repair stage, maximum torque and torsional stiffness) were highest in the COMB-4 group (see Table 2 and FIG. 2).

TABLE 2

Biomechanical properties of healed fractures at day 42 (from Torsion test, mean ± S.D.)

| Group | Fracture Repair Stage (I, II, III or IV)* | Maximum Torque (Nmm) | Torsional Stiffness (Nmm/Deg.) |
| --- | --- | --- | --- |
| Control (n = 7) | 2.4 ± 0.5 | 283.3 ± 108.8 | 46.8 ± 27.6 |
| Tadalafil (n = 10) | 2.4 ± 0.5 | 326.8 ± 138.0 | 59.9 ± 31.1 |
| COMB-4 (n = 9) | 2.8 ± 0.8 | 421.3 ± 114.8 | 89.9 ± 37.2 |

*Fracture Repair Stage numerical conversion: I = 1, II = 2, III = 3, IV = 4

This COMB-4 group surprisingly exhibited 46% higher maximum strength (p=0.093) and 92% higher stiffness (p=0.016) than those of the control group. The tadalafil group exhibited 15% higher maximum strength and 28% higher stiffness with respect to the control group, but this change was not statistically significant.

All of the fractures healed at day 42 and were greater than Stage II of the biomechanical classification of fracture repair. Stage IV fracture repairs were not seen in the tadalafil, nor in the control groups, but were seen in 22% of the COMB-4 treatment group.

The remaining fractures in the three groups were either Stage II or Stage III (see Table 2).

Figure 5:
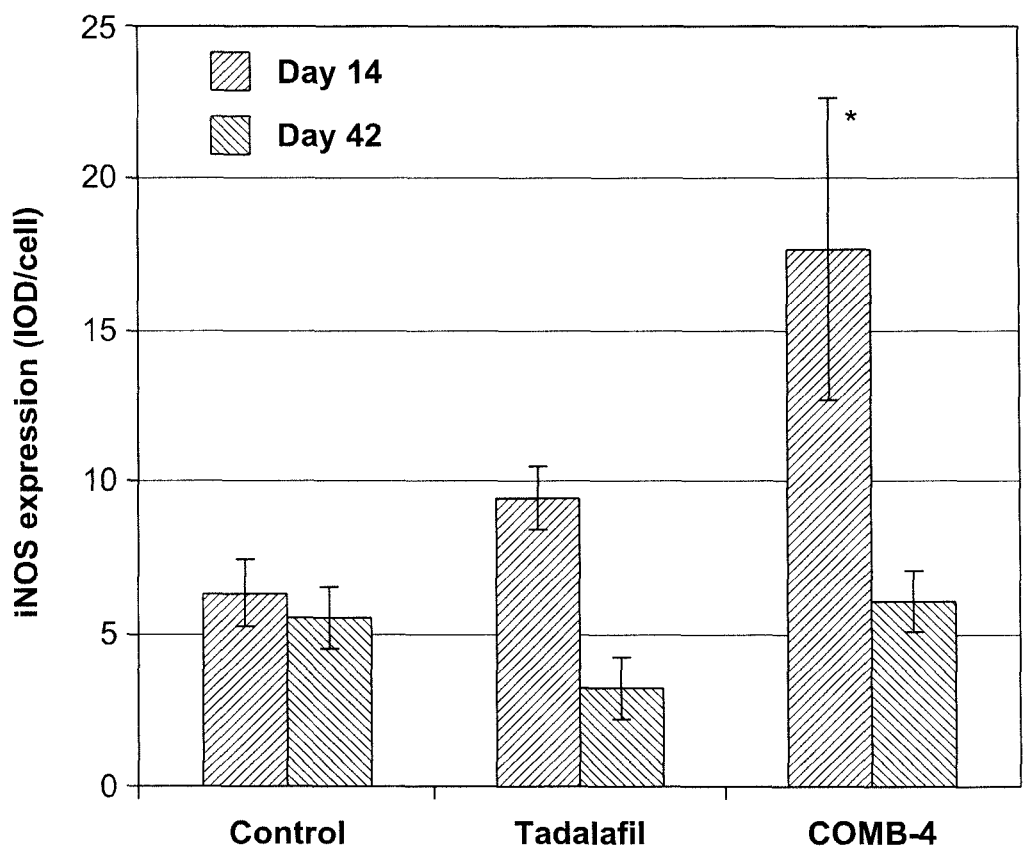
FIG. 5 shows the effect of tadalafil and COMB-4 (the nutraceutical composition of the present invention) on iNOS expression at day 14 and day 42 after femoral fracture. The expression of iNOS was determined by immunohistochemistry at 14 days or 42 days after fracture and treatment with tadalafil or COMB-4 beginning daily immediately after fracture. Quantitative Image analysis of the intensity per cell is shown, and results are expressed as mean±S.E.*$p<0.05$ compared to control group.

Expression of iNOS in Fracture Healing. At 14 days post-fracture, iNOS expression measured at the callus level was significantly increased in the tadalafil and the COMB-4 groups as compared to the control group, while at day 42, iNOS expression in all three groups, as expected, had returned to baseline values (see FIG. 5).

The foregoing experiments were designed to determine whether prolonged upregulation of the NO-cGMP pathway via iNOS begun immediately following a fracture would enhance the fracture healing process. This hypothesis was built on the observation that a) NO is involved in fracture healing as evidenced by the induction of all three isoforms of NOS in a specific sequential manner during the fracture healing process) iNOS is known to be expressed in different tissues in response to an injury, and its induction in such injured tissues is considered a protective mechanism against abnormal wound healing). iNOS is the first NOS isoform induced immediately and rapidly following a fracture but then tapers off after peaking around the one to two week mark. iNOS is most intimately involved with osteoblast function and bone formation.

Furthermore, although inhibition of all three NOS enzymes will result in retardation of both bone formation and normal fracture healing, it has been shown that the specific targeted inhibition or deletion of the iNOS enzyme will negatively impact the fracture healing process while replacement of the deficient iNOS gene to iNOS deficient animals will result in normal fracture healing.

As discussed above, Phosphodiesterase (PDE) inhibitors are compounds that can upregulate iNOS via the NO-cGMP pathway, and have been reported to enhance fracture healing as well as promote the differentiation of osteogenic precursor cells to osteoblasts. However, after 42 days of daily tadalafil, fracture healing, as measured by either the biomechanical fracture repair stage, maximum torque or torsional stiffness, was not significantly enhanced when compared to the controls.

In contrast, COMB-4 had surprising benefits for bone fracture healing. COMB-4 comprises a mixture of L-citrulline, ginger, *Muira puama* and *Paullinia cupana*, and significantly enhances fracture healing as measured by both the fracture repair stage and torsional stiffness. With regard to maximum toque, COMB-4 showed a value 46% greater than the control and 29% greater than the tadalafil group. This suggests there is a tendency toward improvements in maximum toque strength over time. The smaller mineralized callus volume and the newly mineralized callus seen in these COMB-4 animals may be indicative of a faster remodeling of bridging callus that contributes to the superior biomechanical properties of the COMB-4 group compared to both the tadalafil and control groups.

The benefits of the present invention in treating bone fracture has been demonstrated by the foregoing experiments, which is the first randomized, blinded control study that demonstrates in mammals the efficacy of a natural product in enhancing the functional strength of bone following a fracture. COMB-4 by itself resulted in excellent biomechanical properties associated with fracture healing when compared to that seen with either the control or tadalafil Group. L-citrulline, *Muira puama, Paullinia cupana* and ginger, the constituents of COMB-4, are known in humans to have an innocuous side effect profile. L-arginine can be used to partially or totally replace L-citrulline, although L-citrulline is preferred due to its bioavailability inter alia.

In an embodiment, a PDE inhibitor, such as but not limited to tadalafil, is combined with a composition comprising COMB-4, and administered to a human or other mammal in a pharmaceutically effective amount for a sufficient period of time after bone fracture to enhance healing of the bone fracture. In another embodiment COMB-4 is used by itself; this is of particular benefit to patients that do not tolerate PDE inhibitors.

Treatment of bone fracture in accordance with the present invention includes repeated administration of the nutraceutical compositions of the present inventions to a patient over a period of time sufficient to obtain the desired result. One of ordinary skill in the art will recognize that dosages administered in the rat model are scaled to the size of the mammal (e.g., human) receiving the dosage. While the COMB-4 nutraceutical composition can be administered as a single composition, its individual ingredients can be given separately during each periodic administration for a sufficient duration of time to have the desired benefit for bone fracture healing.

Method and Composition for the Treatment and Prevention of Osteoporosis

In addition to the use of the nutraceutical composition of the present invention in the treatment of fractures, the present invention provides a nutraceutical composition for the treatment and/or prevention of osteoporosis.

The present nutraceutical composition reflects the ability of a combination of ginger, *Muira puama, Paullinia cupana* (guarana), and L-citrulline and/or L-arginine to treat and/or prevent osteoporosis, and even reverse physiological processes that cause osteoporosis, so that the beneficial results may continue for a period of time after administration. The nutraceutical composition may be taken for an indefinite period to sustain the beneficial effects and/or to postpone or reduce progression of osteoporosis.

As mentioned above, and in accordance with a preferred embodiment, the total daily dosage of the nutraceutical composition is
- up to about 3 g (preferably about 250 mg to about 2 g) ginger or ginger derivative,
- about 10 mg to about 2 g (preferably about 400 mg to about 2 g) of a L-citrulline, L-arginine or a combination of L-arginine and L-citrulline,
- about 100 mg to about 3 g (preferably about 500 mg to about 1.5 g) *Muira puama*, and
- at least about 125 mg (preferably about 500 mg) *Paullinia cupana* (guarana).

A specific individual dosage forming the basis for the test results presented herein, where the nutraceutical composition is taken only once a day, includes
- about 500 mg ginger or ginger derivative,
- about 1,600 mg L-citrulline,
- about 500 mg *Muira puama*, and
- about 500 mg *Paullinia cupana*.

While a simple daily administration of the nutraceutical composition of the present invention was used during testing, it is appreciated the nutraceutical composition may be administered multiple times a day and the individual dosages would therefore be adjusted so as to not exceed the preferred total daily dosage as outlined above. Whether the nutraceutical composition is administered once a day or multiple times throughout the day, the nutraceutical composition is administered for a sufficient period of time to treat and/or prevent osteoporosis. In addition, *Paullinia cupana* formulations used in making compositions of the present inventions may optionally include caffeine.

The nutraceutical composition may include optional pharmaceutically acceptable excipients, fillers, binders, and colorants, and can be packaged in standard gelatin capsules or formed into solid tablets, taken in particulate form, or mixed into and/or suspended in solution.

The present nutraceutical composition reflects the ability of a combination of ginger, *Muira puama, Paullinia cupana* (guarana), and L-citrulline and/or L-arginine to treat and/or prevent osteoporosis. The nutraceutical composition may be taken for an indefinite period to sustain the beneficial effects.

According to another aspect of the present invention, an oral dosage form comprises a nutraceutical composition in accordance with the present invention, wherein the dosage form is selected from the group consisting of a tablet, capsule, lozenge, powder or suspension comprising the foregoing ingredients. Preferred suspensions are aqueous and/or alcohol (ethanol) based.

Considering now the mechanisms by which the present nutraceutical composition works, it has been described above that nitric oxide (NO) is known to be an important signaling molecule in many physiological systems.

With the foregoing in mind, the present nutraceutical composition composed of (1) ginger or ginger derivative, (2) L-citrulline, L-arginine, or mixture of L-arginine and L-citrulline, (3) *Muira puama*, and (4) *Paullinia cupana* is useful in the treatment and/or prevention of osteoporosis. This nutraceutical composition results in an upregulation of the nitric oxide-cGMP pathway which results in the treatment and/or prevention of osteoporosis.

As shown in FIG. 1, and as discussed above, there are three mechanisms for the upregulation of the nitric oxide-cGMP pathway.

Figure 6:
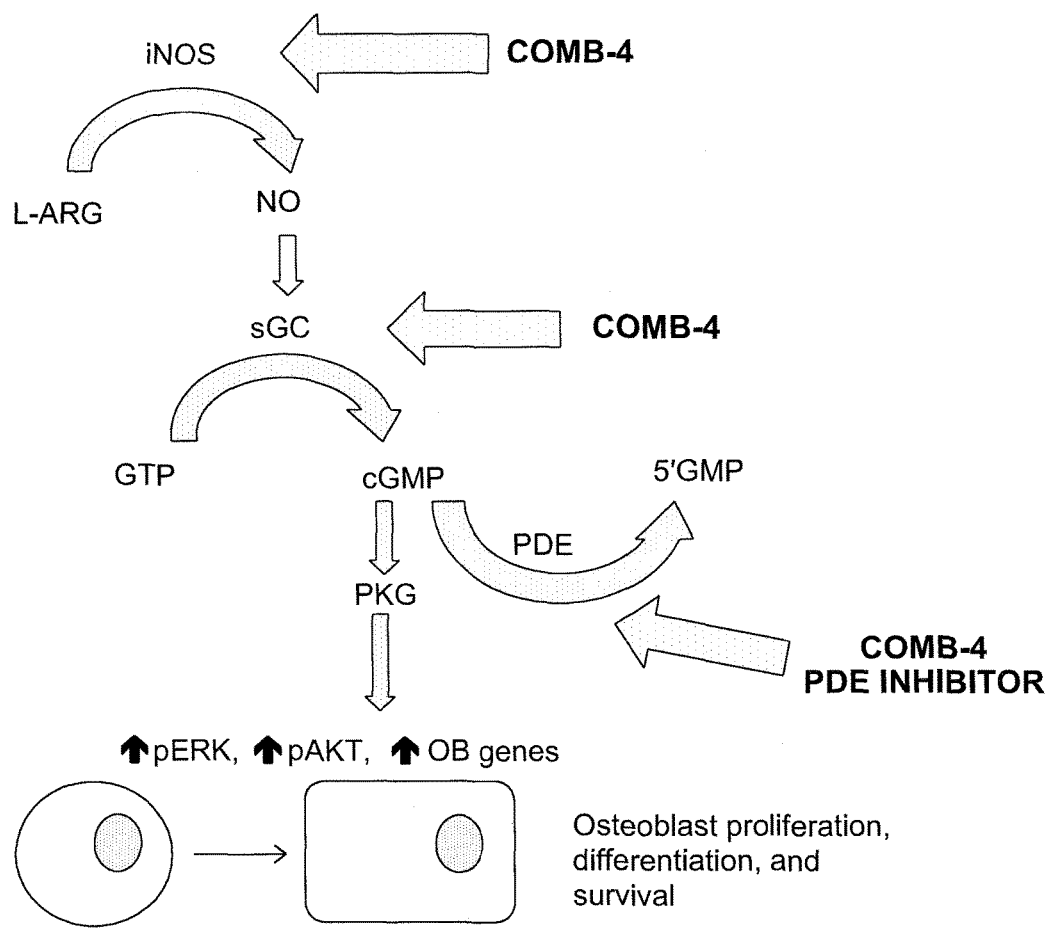
FIG. 6 is a schematic representation of the biological pathways upon which the present composition acts in order to up-regulate the nitric oxide-cGMP pathway for the purpose of treating osteoporosis.

With reference to FIG. 6, the present invention focuses upon osteoblasts, which are cells intimately involved in bone metabolism. Osteoblasts, among other roles that are not fully understood, secrete the matrix for bone formation. The nutraceutical composition of the present invention increases the nitric oxide-cGMP pathway by increasing nitric oxide production and decreasing the conversion of cGMP to 5'GMP. This results in an increase in osteoblast proliferation, differentiation and survival by increasing pERK (Phosphorylated Extracellular Signal-Regulated Kinase), pAKT (Phosphorylated AKT (Protein kinase B), and OB genes (Obese Genes).

Figure 7:
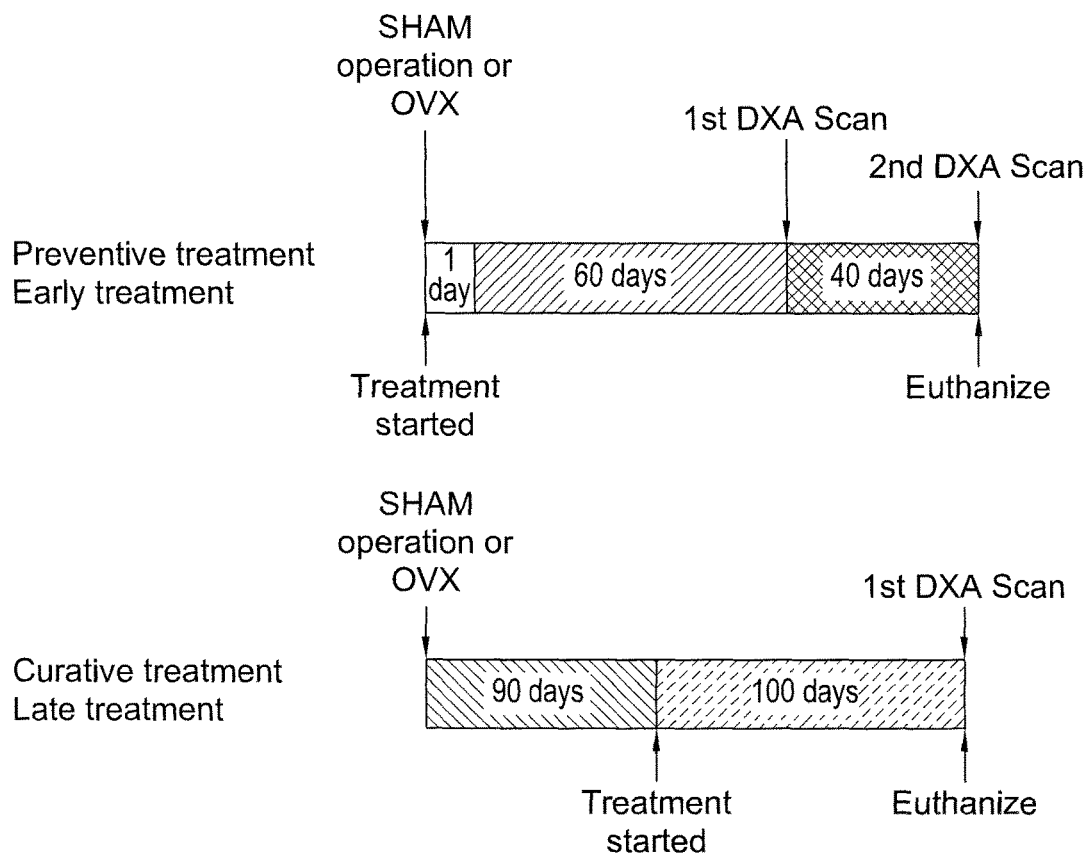
FIG. 7 is a schematic representation of the experimental design employed in accordance with testing the efficacy of the present composition in the treatment of osteoporosis.
Figure 8:
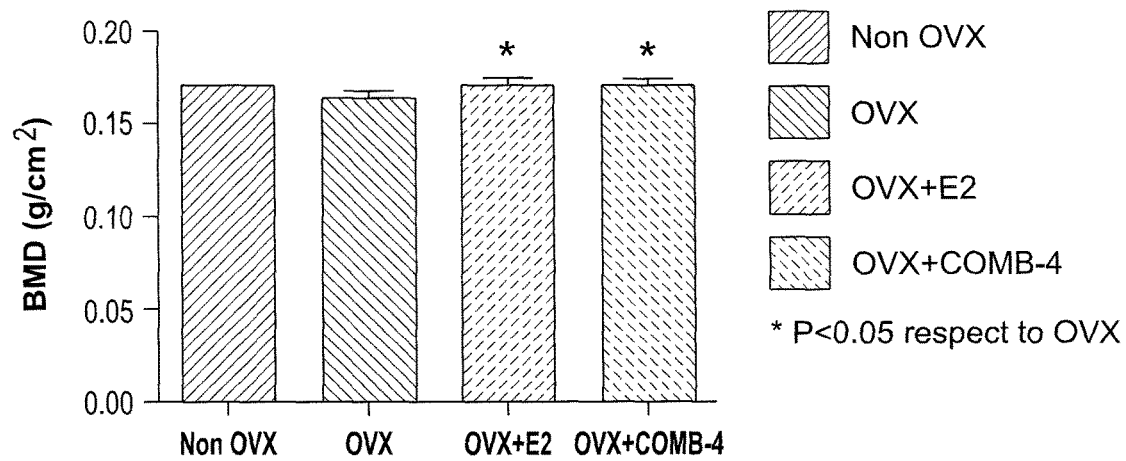
FIGS. 8-27 present test data supporting the efficacy of the present composition in the treatment of osteoporosis.
Figure 9:
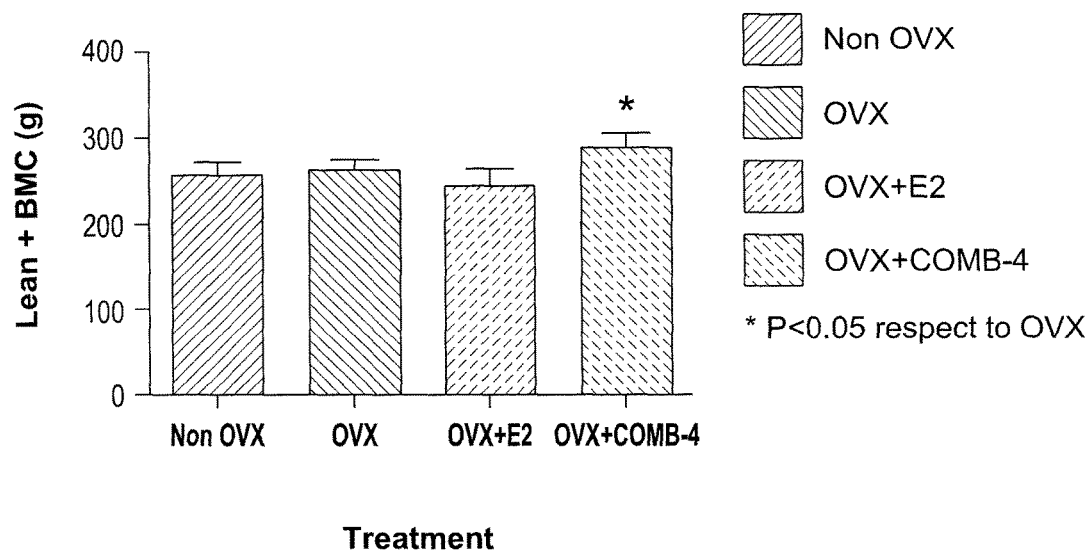
Figure 10:
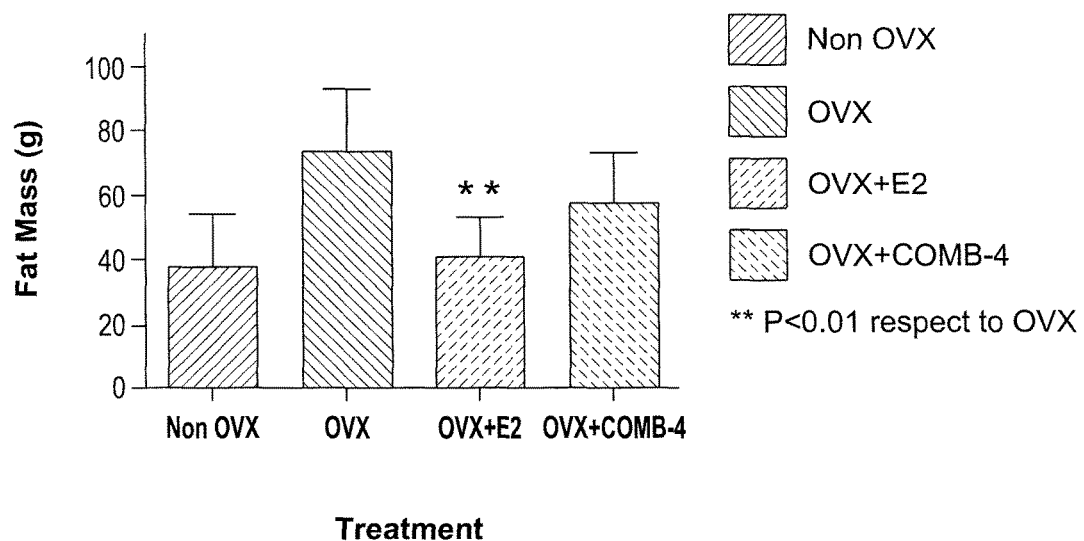
Figure 11:
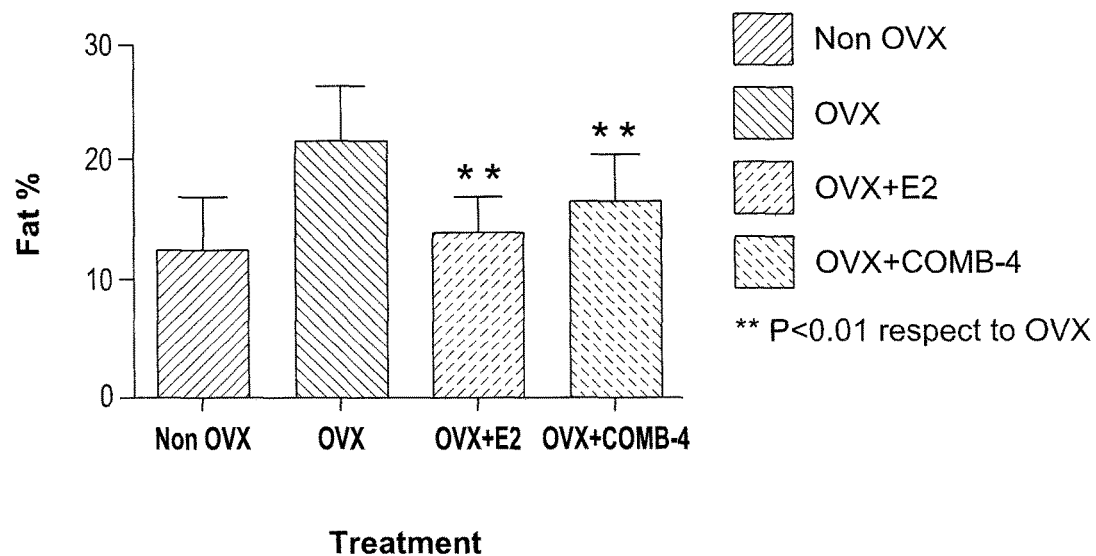
Figure 12:
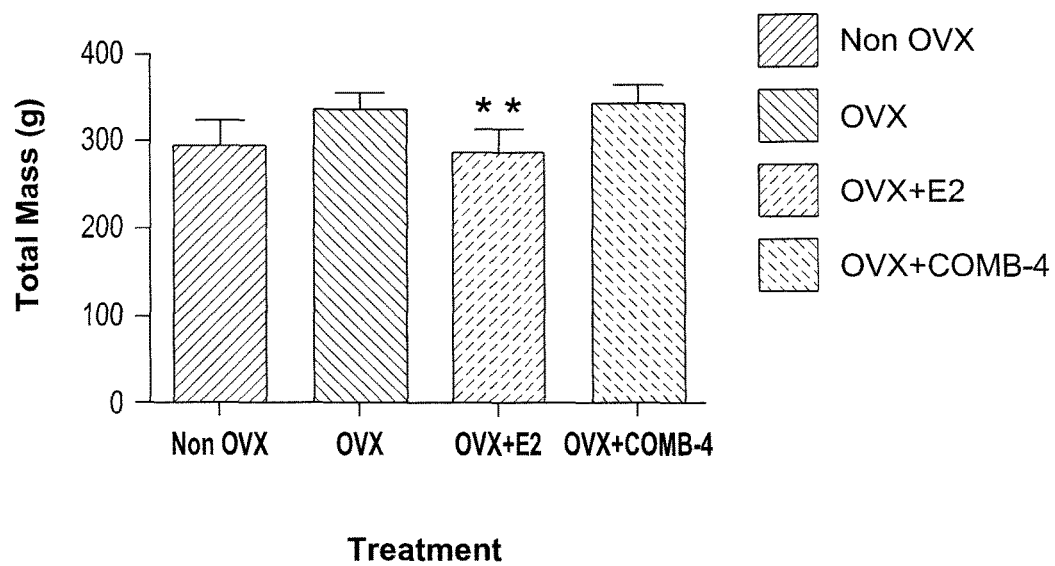
Figure 13:
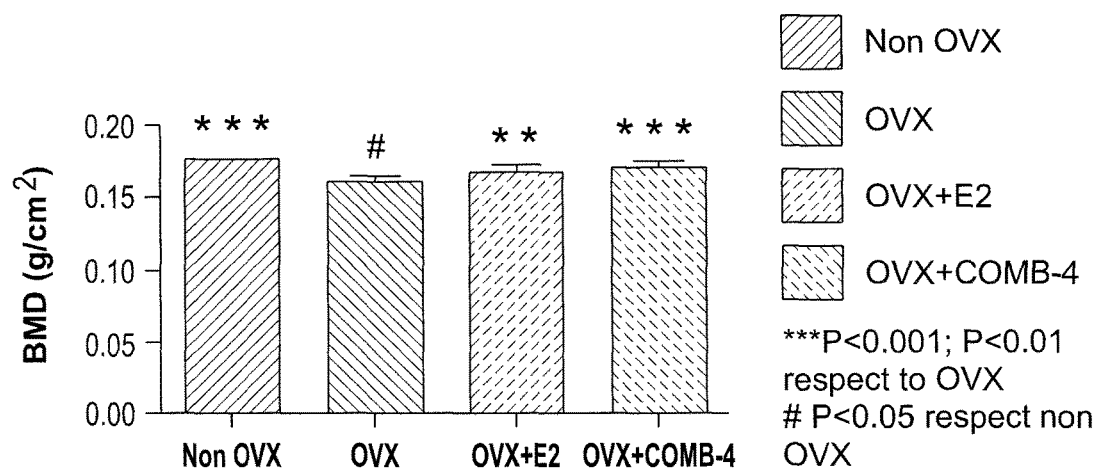
Figure 14:
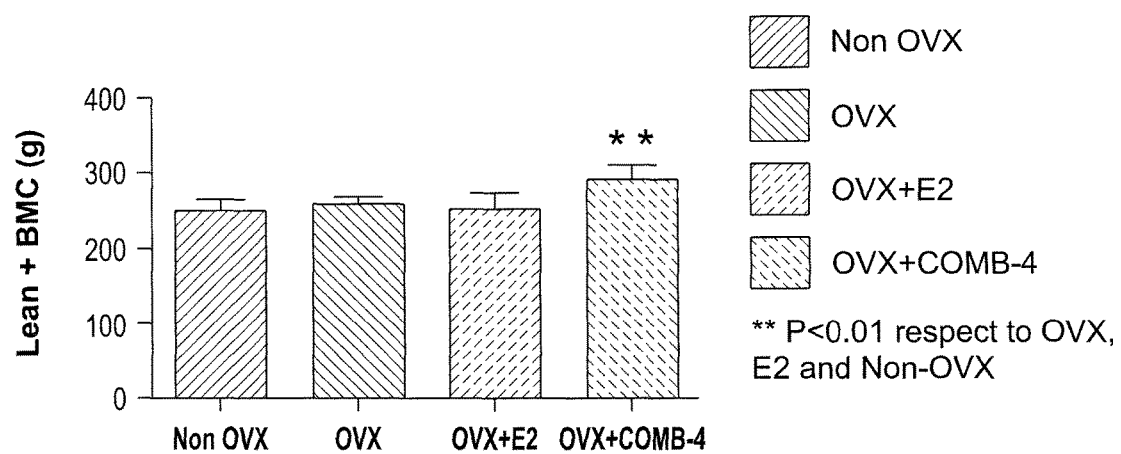
Figure 15:
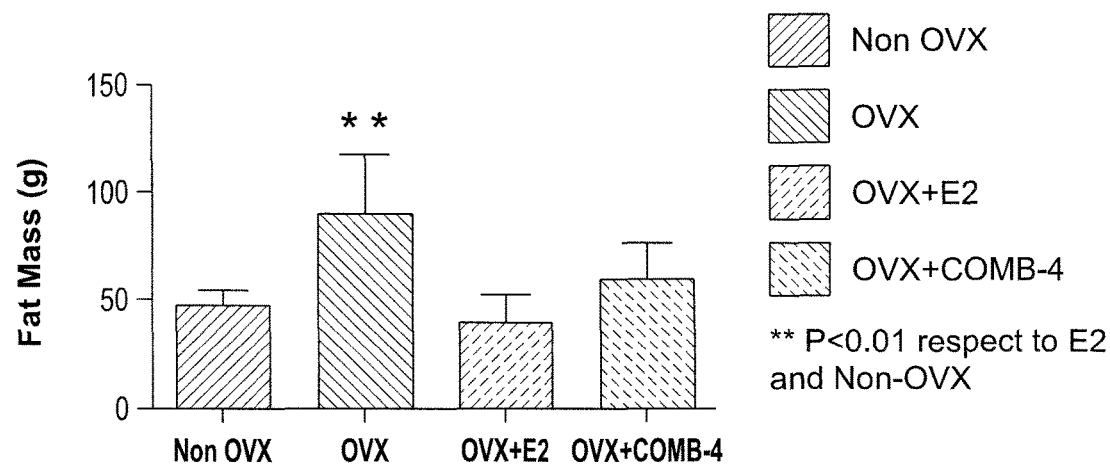
Figure 16:
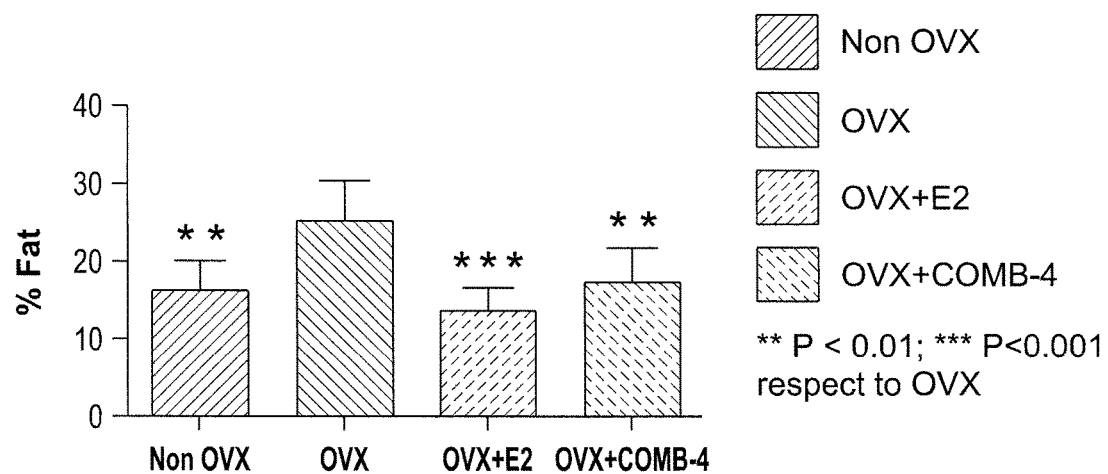
Figure 17:
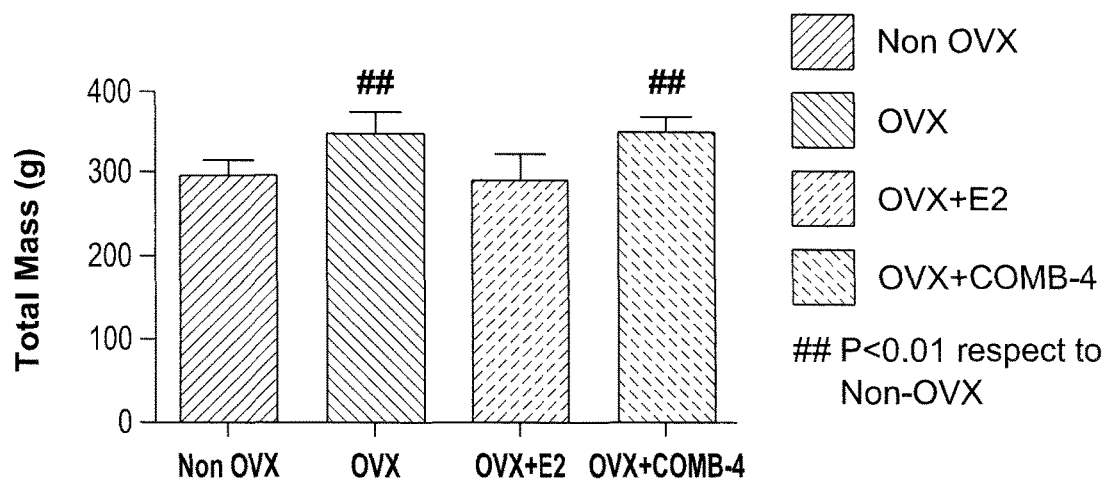
Figure 18:
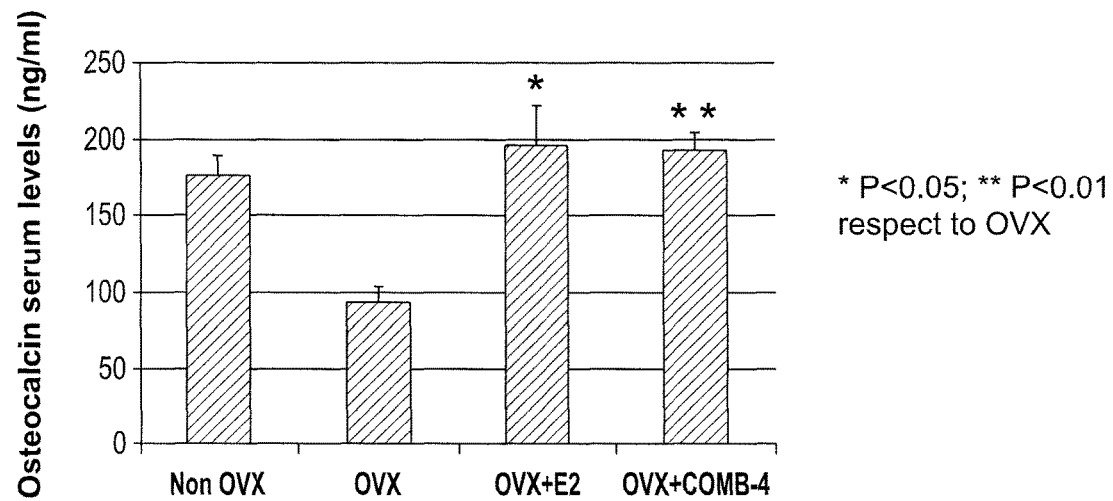
Figure 19:
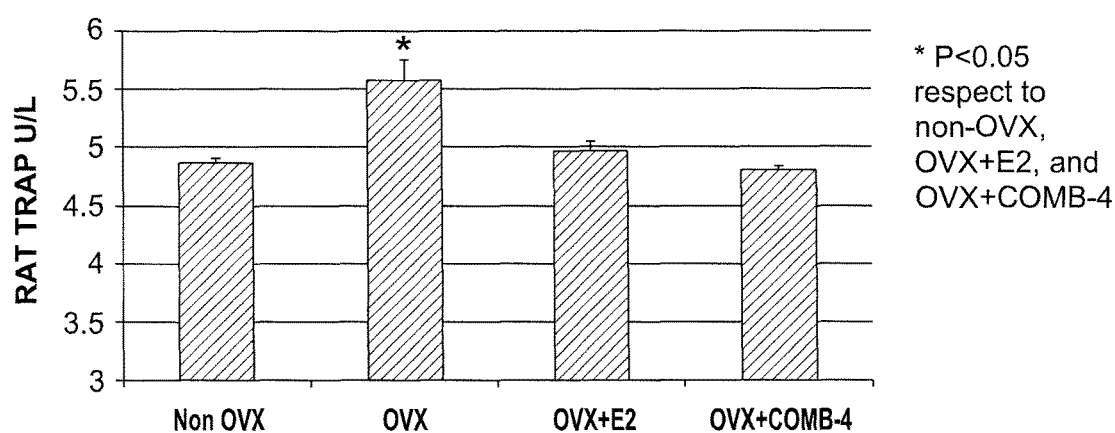
Figure 20:
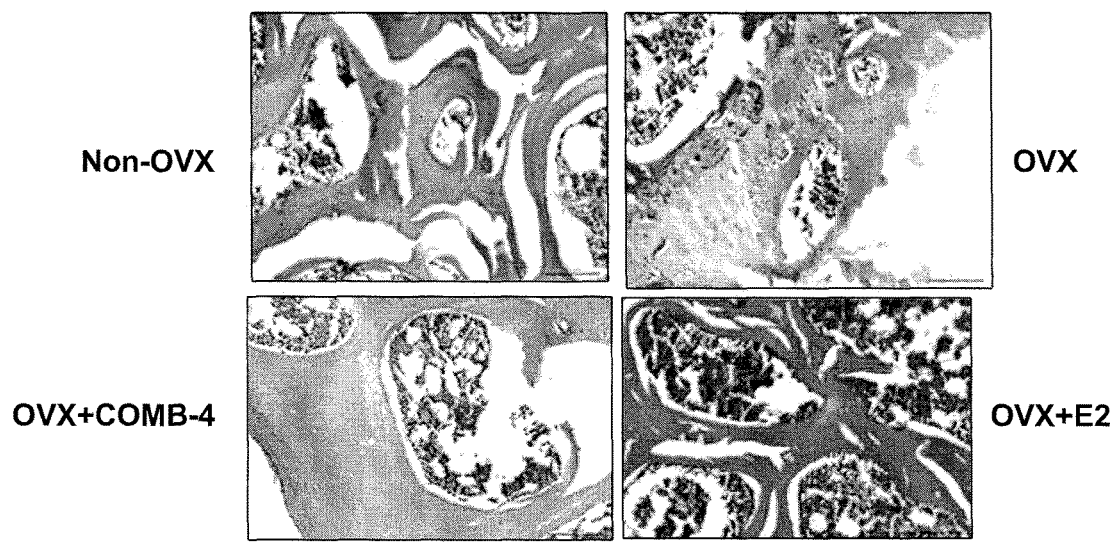
Figure 21:
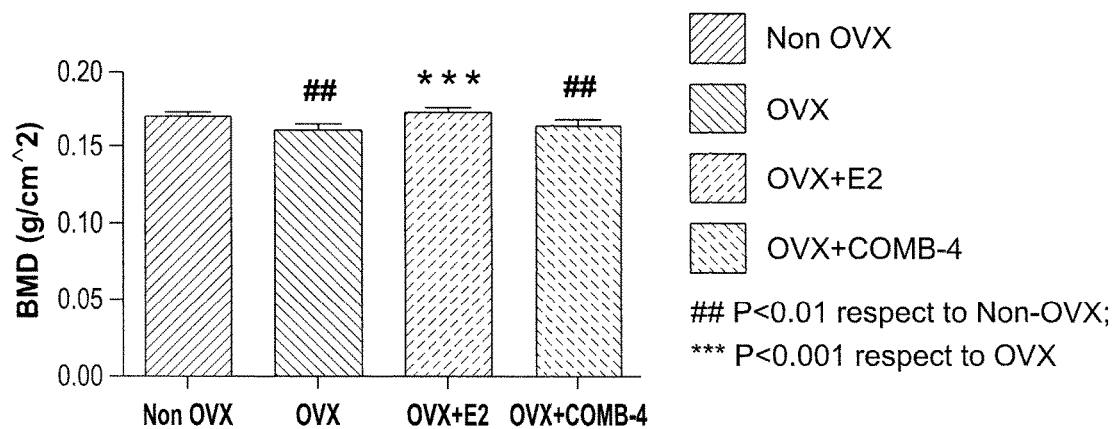
Figure 22:
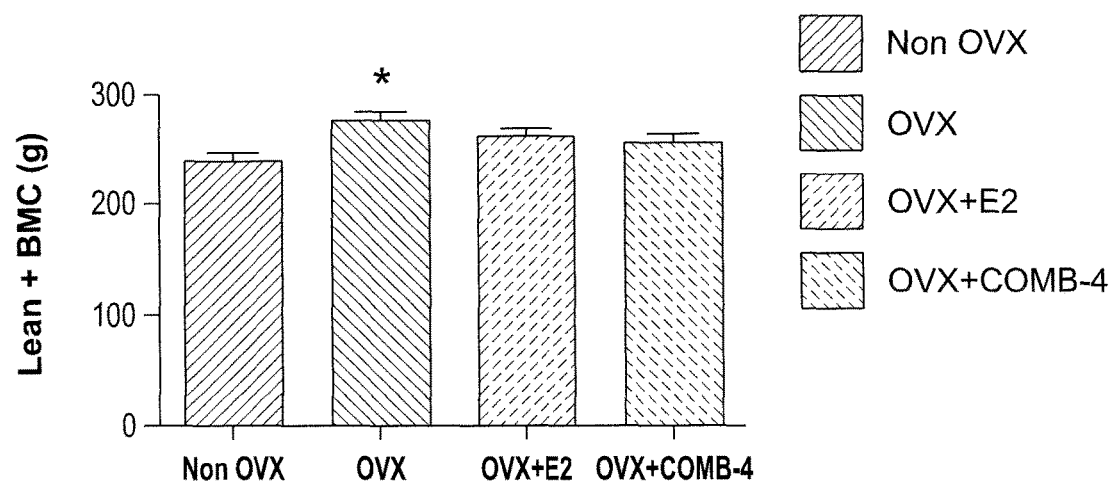
Figure 23:
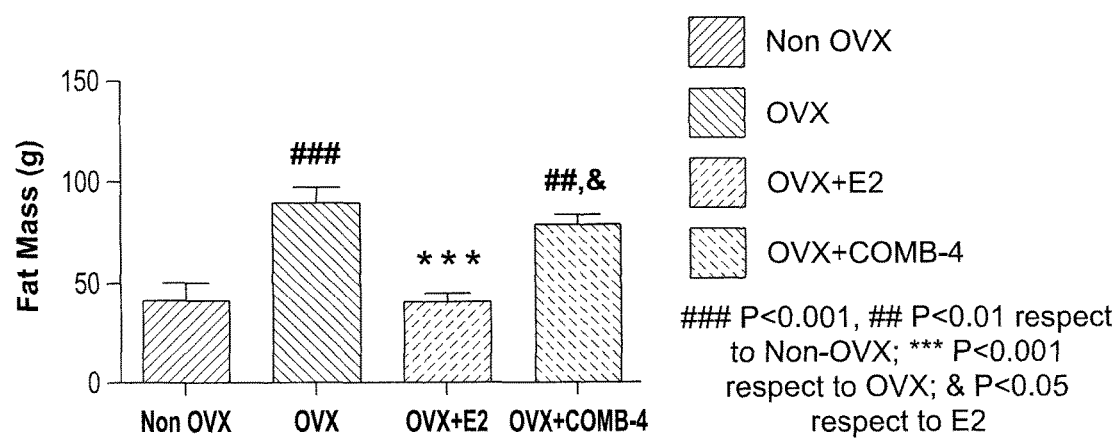
Figure 24:
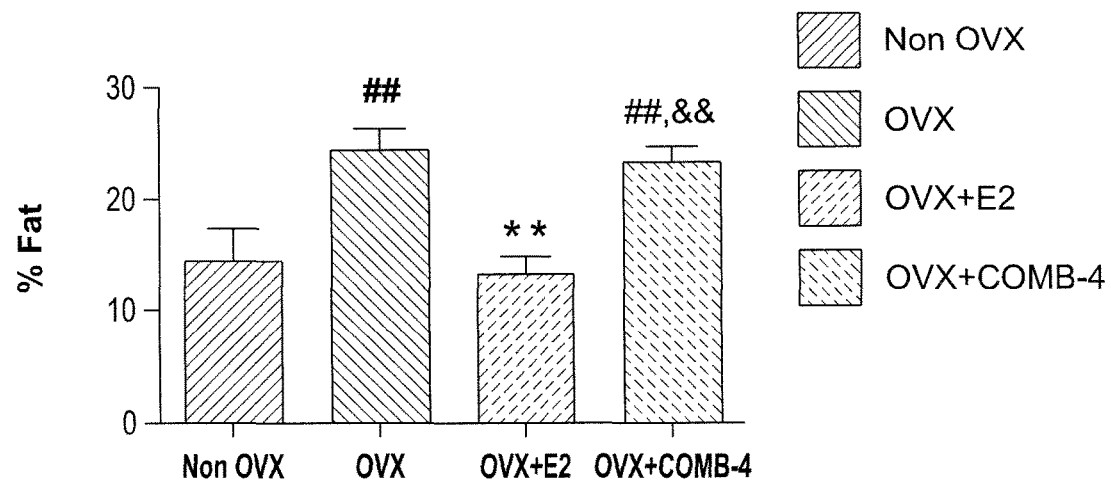
Figure 25:
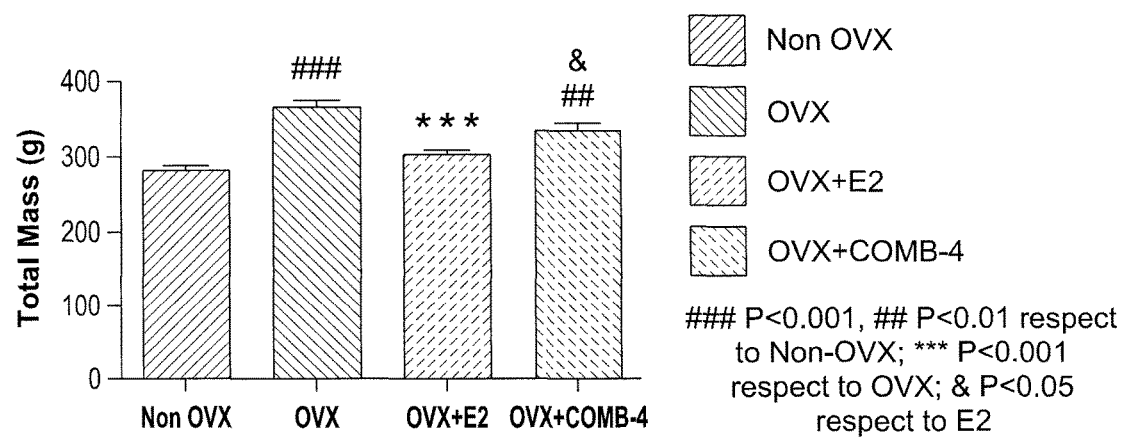
Figure 26:
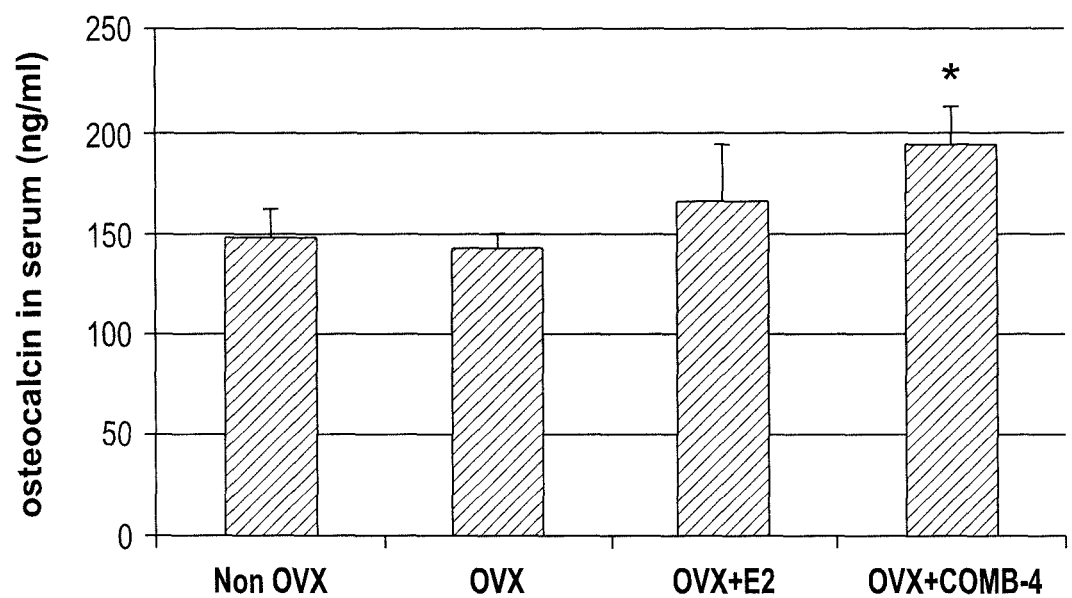
Figure 27:
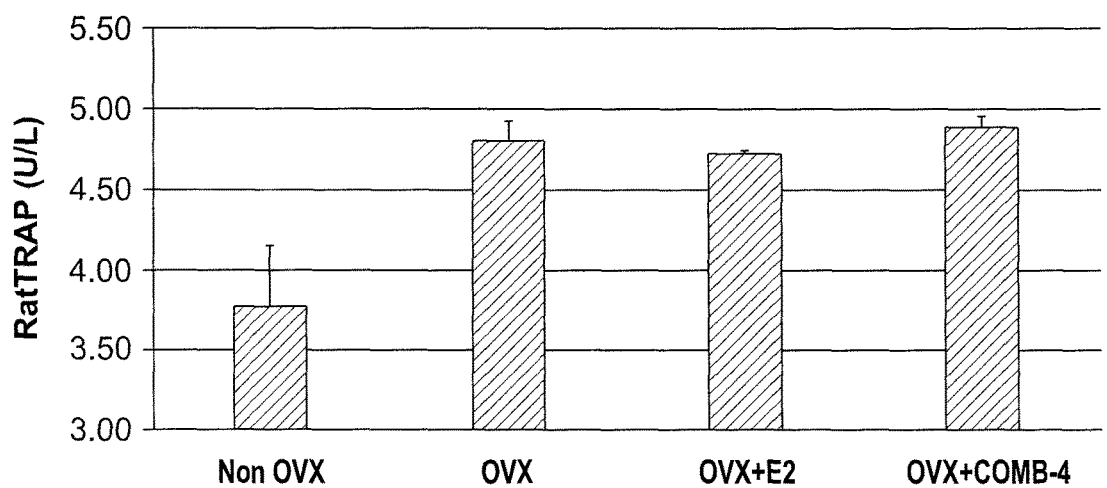
Figure 28:
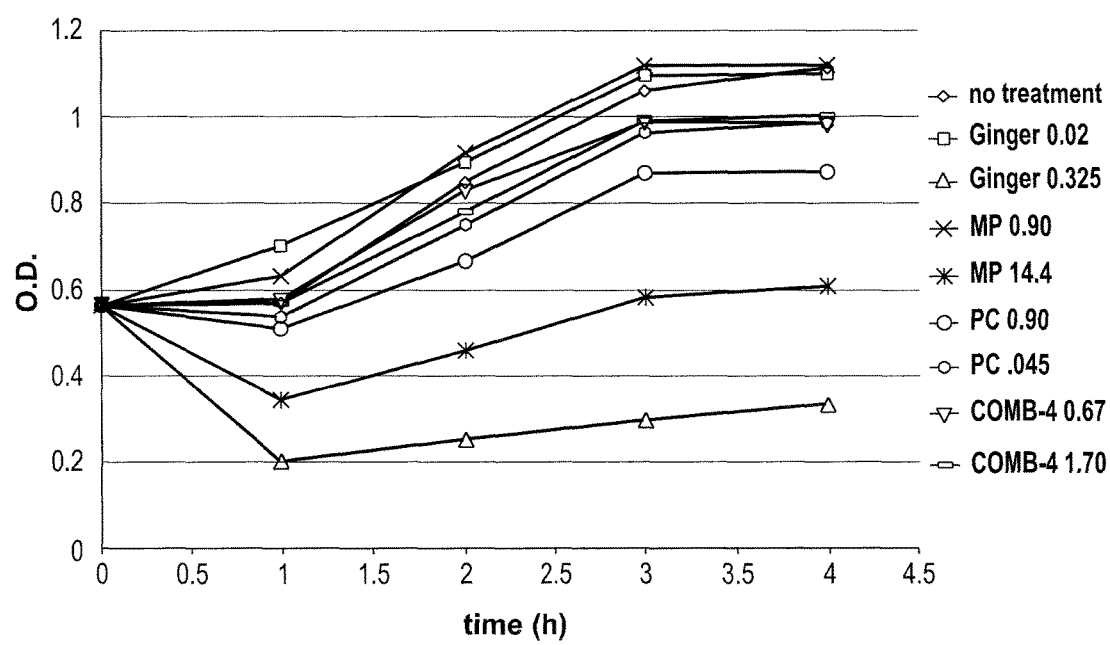
FIGS. 28-32 present data demonstrating that the present composition, in dosages used in the in vivo study, do not have an inhibitory effect on the proliferation of osteoblasts.
Figure 29:
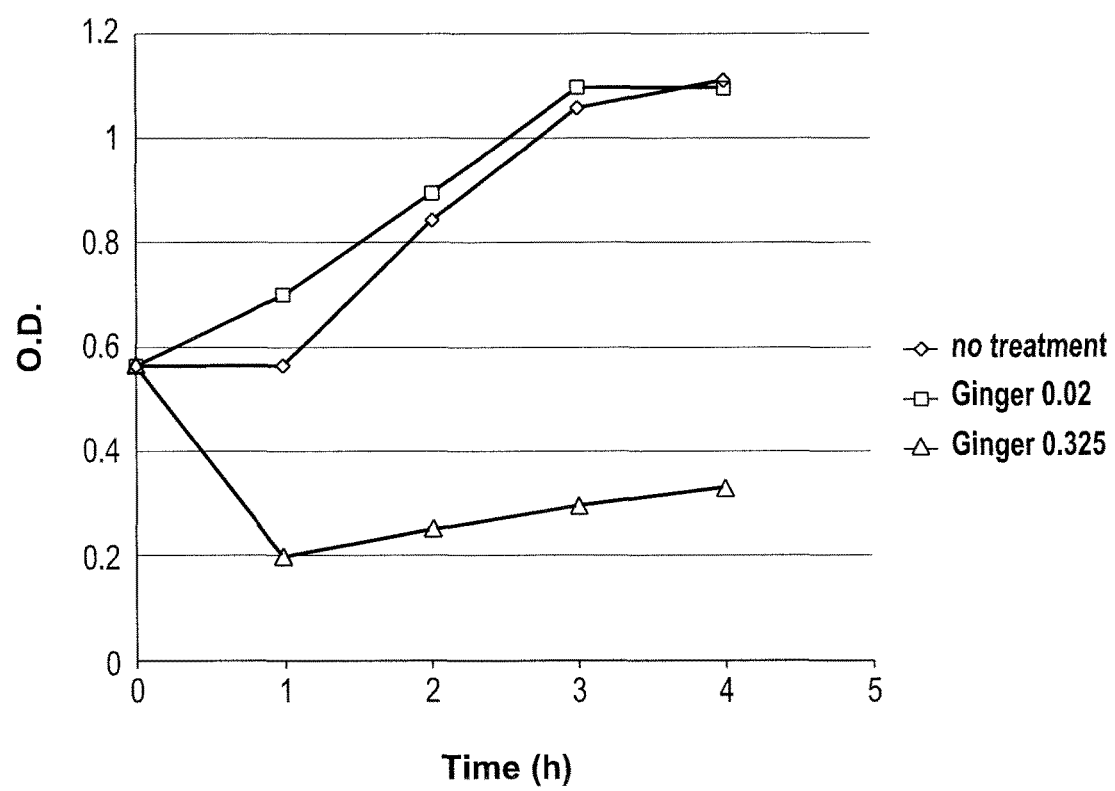
Figure 30:
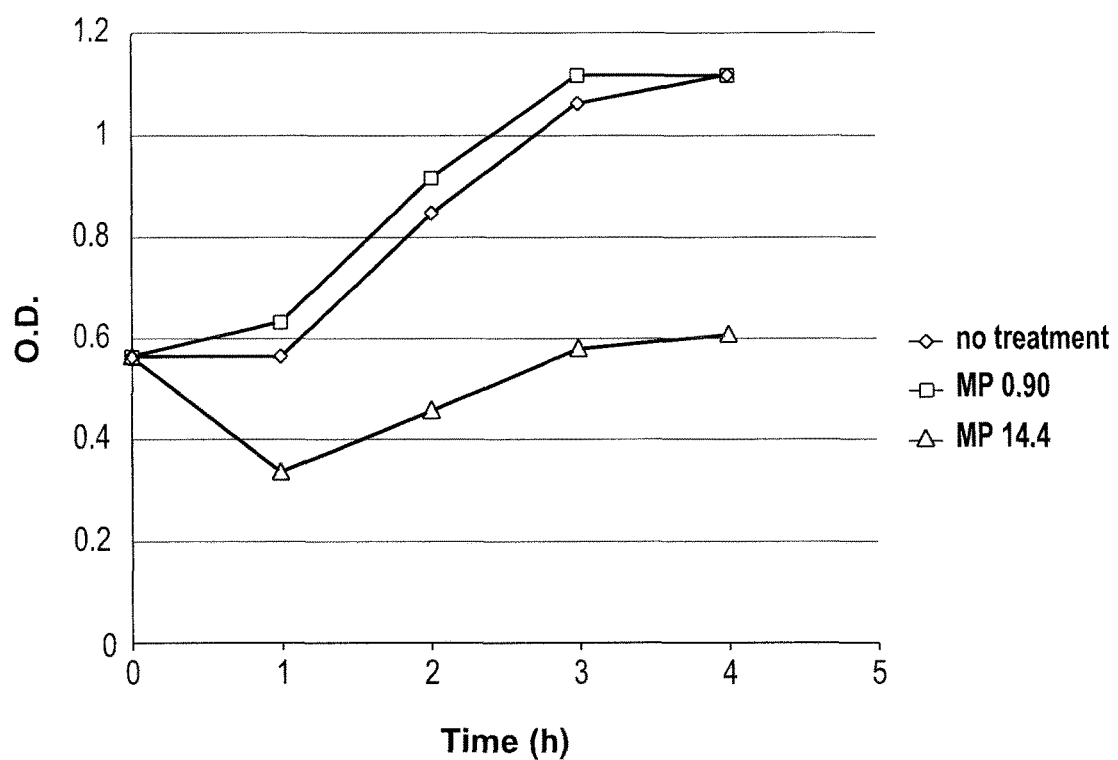
Figure 31:
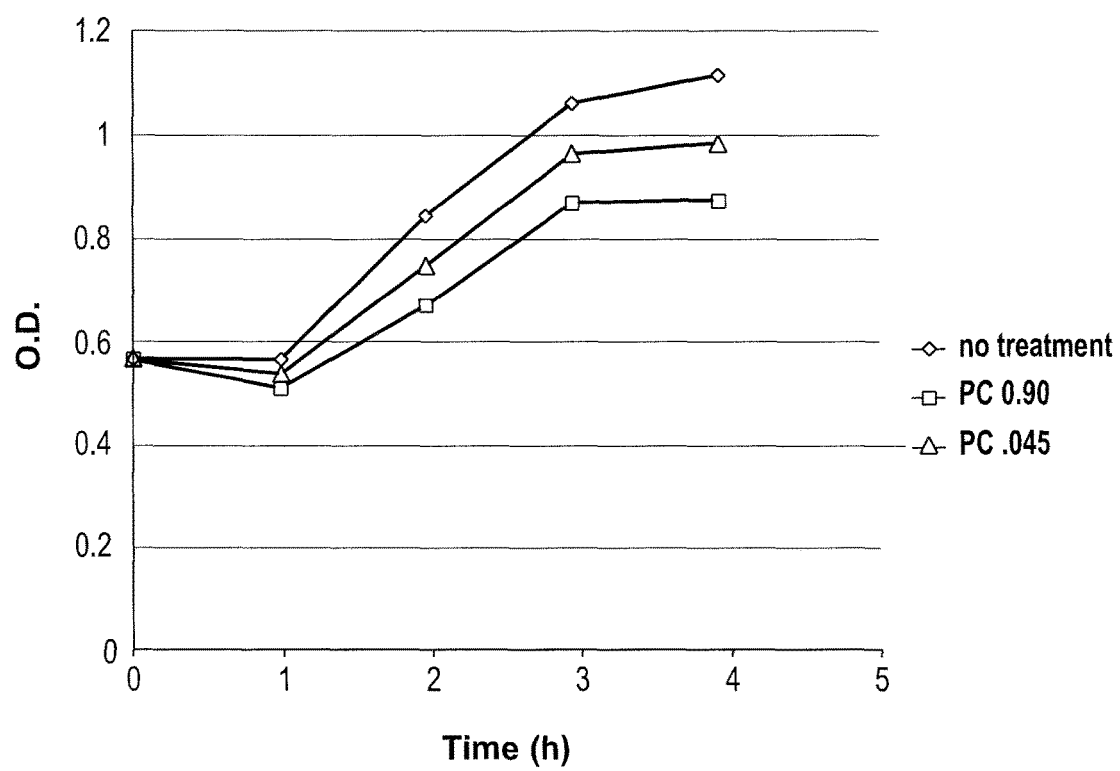
Figure 32:
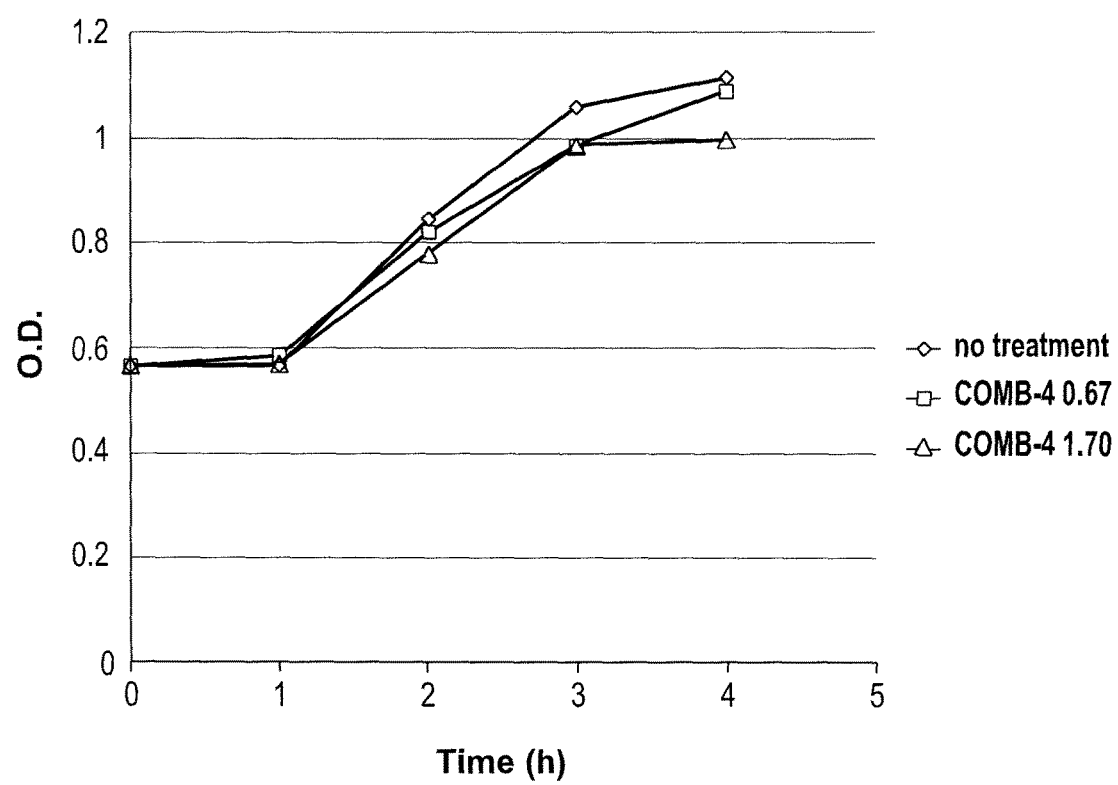

As shown in FIG. 7, the experimental design used in establishing the efficacy of the present nutraceutical composition in the treatment of osteoporosis included treatment of 6 month old Sprague Dawley retired breeder rats with either a preventative treatment with the application of the nutraceutical composition starting on the first day of the experiment or a curative treatment with the application of the nutraceutical composition starting 90 days after the start of the experiment.

In accordance the preventative treatment with the application of the nutraceutical composition starting on the first day of the experiment, a SHAM operation or an Ovariectomy (OVX) was also performed on the first day of the experiment. A $1^{st}$ DEXA (Dual-Energy X-ray Absorptiometry) Scan was performed after 60 days of treatment and then again after 100 days of the treatment. In accordance the curative treatment, a SHAM operation or an Ovariectomy (OVX) was performed on the first day of the experiment and application of the nutraceutical composition was not started until 90 days after the start of the experiment. For comparative purposes, the rats were similarly treated with Estradiol (E2), a composition known for use in the treatment of osteoporosis. Thereafter, a $1^{st}$ DEXA Scan was performed 190 days after the start of the experiment (or 100 days after the start of treatment with the nutraceutical composition).

The rats were studied via DEXA Scan to determine BMD, LEAN (lean tissue excluding fat)+BMC (Bone Mineral Content), FAT and % FAT. In addition, bone markers in serum (in particular, osteocalcin and TRAP5c) were studied and quantified.

The charts shown in FIGS. 8 to 27 summarize the data, which establishes the efficacy of the nutraceutical composition in the treatment and prevention of osteoporosis.

Further testing, as summarized via the graphs shown in FIGS. 28 to 32 support the conclusion that the nutraceutical composition of the present invention is not toxic to the proliferation of osteoblasts, whereas ginger (see FIG. 29) and *Muira puama* (see FIG. 30), two of the four components found in COMB-4, are in fact toxic to the proliferation of osteoblasts when the osteoblasts are exposed to these two components on an individual basis at doses contained in COMB-4. The testing was done by studying the optical density (OD) of a cell culture of osteoblasts for a period time after the administration of three of the four compositions at various doses. For example, ginger, *Muira puama*, *Paullinia cupana* (guarana), and the nutraceutical composition (COMB-4) were tested at various concentrations. In particular, the following concentrations were tested to determine their effect on cell proliferation: ginger at concentrations of 0.02 mg/ml and 0325 mg/ml (Ginger 0.02 & Ginger 0.325, as respectively designated in the FIGS. 28 and 29); *Muira puama* (MP) at concentrations of 0.90 mg/ml and 14.4 mg/ml (MP 0.90 & MP 14.4, as respectively designated in the FIGS. 28 and 30); *Paullinia cupana* (PC) at concentrations of 0.90 mg/ml and 0.045 mg/ml (PC 0.90 & PC 0.045, as respectively designated in the FIGS. 28 and 31); and the nutraceutical composition (composed of 500 mg ginger or ginger derivative, about 1,600 mg L-citrulline, about 500 mg *Muira puama*, and about 500 mg *Paullinia cupana*) at concentrations of 0.67 mg/ml and 1.70 mg/ml (COMB-4 0.67 & COMB-4 1.70, as respectively designated in the FIGS. 28 and 32).

The nutraceutical composition of the present invention prevented a decrease in BMD in tandem with an increase in serum osteocalcin and a decrease in TRAP-5 (Tartrate-Resistant Acid Phosphatase). As a result, the nutraceutical composition of the present invention may be used to treat and/or prevent osteoporosis. Treatments can consist of either short term self-administered oral dosages taken periodically (e.g., at least once a day or other period of time in between dosages until the desired effect is reached or as part of an individual's long-term, even lifetime as daily nutrition).

It is appreciated the nutraceutical composition of the present invention for the treatment of osteoporosis may further include other compounds, but ginger, *Muira puama*, and *Paullinia cupana* and L-arginine or L-citrulline are essential in the composition and its ability to treat osteoporosis.

As discussed above, preferred total daily dosage of ginger in the nutraceutical composition of the present invention comprise between about 250 mg to about 2 g. The total daily dosage of the nutraceutical composition of the present invention further comprises about 10 mg to about 2 g L-citrulline About 10 mg to about 2 grams L-arginine can be used in place of and/or in addition to L-citrulline. However, since it has been discovered that a larger amount of in vivo L-arginine for use in endogenous production of nitric oxide can be induced by a smaller dosage of L-citrulline than of oral L-arginine, preferred compositions of the present invention include L-citrulline in place of and/or in addition to L-arginine (see Schwedhelm et al., *British Journal of Clinical Pharmacology*, 65: pp 51-59, (2007)). Still further, the total daily dosage of *Muira puama* in the nutraceutical composition of the present invention is about 100 mg to about 3 g (preferably about 500 mg to about 1.5 g) and the total daily dosage of *Paullinia cupana* (guarana) in the nutraceutical composition of the present invention is at least about 125 mg (preferably about 500 mg). With this in mind, and as discussed above, an individual dosage, where the nutraceutical composition is taken only once a day, includes about 500 mg ginger or ginger derivative, about 1,600 mg L-citrulline, about 500 mg *Muira puama*, and about 500 mg *Paullinia cupana*. As explained above, it is appreciated that the nutraceutical composition may be administered multiple times a day and the individual dosage would therefore be adjusted so as to not exceed the preferred total daily dosage as outlined above. Whether a single dosage is take each day or multiple doses are taken throughout the day, repeated dosages of compositions of the present inventions are provided over extended periods of time until the desired effect is obtained. Repeated administration of the compositions of the present inventions to patients demonstrating osteoporosis symptoms are made until desired osteoporosis treatment results are obtained, and may be continued thereafter as a prophylactic.

In an embodiment, and as discussed above, an individual dosage, where the nutraceutical composition is taken only once a day, used in accordance with the present invention includes about 500 mg ginger or ginger derivative, about 1,600 mg L-citrulline, about 500 mg *Muira puama*, and about 500 mg *Paullinia cupana*. Whether the nutraceutical composition is administered once a day as disclosed above or the nutraceutical composition is administered is administered multiple times during the course of the day, the nutraceutical composition is administered for a sufficient period of time to treat osteoporosis and achieve desired results. However, testing has shown the quantities of the various elements may be varied and the total daily dosage of the nutraceutical composition may contain up to about 3 g (preferably about 250 mg to about 2 g) ginger or ginger derivative, about 10 mg to about 2 g (preferably about 400 mg to about 3 g) of a L-citrulline, L-arginine or a combination of L-arginine and L-citrulline, about 100 mg to about 3 g (preferably about 500 mg to 1.5 g) *Muira puama*, and at least about 125 mg (preferably about 500 mg) *Paullinia cupana* (guarana). The dosage above may additionally or in place of ginger contain about 20 mg to about 1000 mg 6-gingerol, preferably about 220 mg 6-gingerol, although the present inventors have found it preferable to use ginger.

While details of certain embodiments of the present inventions are described, they are provided as illustrative examples so as to enable those of ordinary skill in the art to practice the inventions. The details provided are not meant to limit the scope of the present inventions, but to be exemplary. Where certain elements of the present inventions can be partially or fully implemented using known constituents, only those portions of such known constituents that are necessary for an understanding and making of the present invention are described, and detailed descriptions of other constituents or formulating processes are omitted as being to simplify explanation of the invention. Further, the present invention encompasses present and future known equivalents to the compositions and methods referred to herein. The inventions are capable of other embodiments and of being practiced and carried out in various ways, and as such, those skilled in the art will appreciate that the conception upon which this disclosure is based may readily be utilized as a basis for the designing of other methods and compositions for carrying out the several purposes of the present inventions.

The invention claimed is:

1. A method for treatment of bone fractures, loss of bone mineral content or bone density, comprising:
    administering a pharmaceutically effective amount of a composition over a sufficient period of time that results in an increase in bone formation and/or prevents a decrease in bone mineral density, wherein the composition comprises ginger or a ginger derivative, *Muira puama*, *Paullinia cupana*, and at least one of the consisting of L-arginine and L-citrulline that stimulates osteoblasts to increases production of NOS, nitric oxide production and cGMP resulting in bone formation.

2. The method according to claim 1, wherein the composition comprises 250 mg to 2 g ginger or ginger derivative.

3. The method according to claim 1, including 10 mg to 3 g of L-arginine, L-citrulline, or a mixture of L-arginine and L-citrulline.

4. The method according to claim 1, including 10 mg to 2 g of L-arginine, L-citrulline, or a mixture of L-arginine and L-citrulline.

5. The method according to claim 1, including 100 mg to 3 g of *Muira puama*.

6. The method according to claim 1, including 500 mg to 1.5 g of *Muira puama*.

7. The method according to claim 1, including at least 250 mg of *Paullinia cupana*.

8. The method according to claim 1, including 500 mg of *Paullinia cupana*.

9. The method according to claim 1, including 250 mg to 2 g of ginger or ginger derivative, 250 mg to 2 g of L-arginine, L-citrulline, or mixture of L-arginine and L-citrulline, 500 mg to 1.5 g of *Muira puama*, and 500 mg of *Paullinia cupana*.

10. The method according to claim 1, wherein administration of the pharmaceutically effective amount of the composition over the sufficient period of time will increase the rate of bone fracture healing.

11. The method according to claim 1, wherein administration of the pharmaceutically effective amount of the composition over the sufficient period of time is effective in treatment of osteoporosis.

* * * * *